US006333031B1

(12) United States Patent
Olsson et al.

(10) Patent No.: US 6,333,031 B1
(45) Date of Patent: *Dec. 25, 2001

(54) RECEPTOR DERIVED PEPTIDES AS MODULATORS OF RECEPTOR ACTIVITY

(75) Inventors: Lennart Olsson, Orinda; Tatjana Naranda, Mountain View, both of CA (US)

(73) Assignee: Reception, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/028,937

(22) Filed: Feb. 24, 1998

Related U.S. Application Data

(63) Continuation-in-part of application No. 08/788,820, filed on Jan. 23, 1997, which is a continuation of application No. 08/701,382, filed on Aug. 22, 1996, now Pat. No. 6,004,758, which is a continuation of application No. 08/612,999, filed on Mar. 8, 1996, now Pat. No. 5,952,293.

(51) Int. Cl.[7] .............................. C07K 7/00; C07K 14/00; C12N 5/06
(52) U.S. Cl. ............................... 424/93.7; 514/4; 514/16; 514/13; 514/12; 514/2; 530/303; 530/328; 530/324; 530/325; 530/350; 435/325
(58) Field of Search ..................................... 530/303, 328, 530/324, 325, 350; 514/2, 4, 12, 13, 16; 424/93.7; 435/325

(56) References Cited

U.S. PATENT DOCUMENTS

| 5,385,888 | 1/1995 | Goodenow et al. . |
| 5,846,827 | * 12/1998 | Celis et al. . |
| 5,885,574 | * 3/1999 | Elliott et al. . |

FOREIGN PATENT DOCUMENTS

| WO 90/08161 | * 7/1990 | (WO) . |
| 90/10016 | 9/1990 | (WO) . |
| 95/05189 | 2/1995 | (WO) . |
| WO 96/03438 | * 2/1996 | (WO) . |

OTHER PUBLICATIONS

Ngo et al. The Protein Folding Problem and Tertiary Structure Prediction, Merz & LeGrand, Birkhauser Boston, pp. 491–495, 1994.*
Salgaller et al. Canc. Immunol. Immunother. vol. 39, pp. 105–116, 1994.*
Silver et al. Nature vol. 360, pp. 367–369, 1992.*
Li et al., "An Irregularity in the Transmembrane Domain Helix Correlates with the Rate of Insulin Receptor Internalization," *Biochemistry*, 33:14333–14338 (1994).
Verhey et al., "Distinct Signals in the GLUT4 Glucose Transporter for Internalization and for Targeting to an Insulin–responsive Compartment," *The Journal of Cell Biology*, 130:1071–1079 (1995).

Hansen et al., "Inhibition of Insulin Receptor Phosphorylation by Peptides Derived from Major Histocompatibility Complex Class I Antigens," *PNAS USA*, 86:3123–3126 (1989).
Olsson et al., "Regulation of Receptor Internalization by the Major Histocompatibility Complex Class I Molecule," *PNAS USA*, 91:9086–9090 (1994).
Stagsted et al., "Inhibition of Internalization of Glucose Transporters and IGF–II Receptors," *The Journal of Biological Chemistry*, 268(30):22809–22813 (1993).
Verland et al., "Specific Molecular Interaction Between the Insulin Receptor and A D Product of MHC Class I," *The Journal of Immunology*, 143(3):945–951 (1989).
Stagsted et al., "Correlation Between Insulin Receptor Occupancy and Tyrosine Kinase Activity at Low Insulin Concentrations and Effect of Major Histocompatibility Complex Class I–Derived Peptide," *The Journal of Pharmacology and Experimental Therapeutics*, 267(2):997–1001 (1993).
Stagsted et al., "A Preformed, Ordered Structure of a 25–Residue Peptide Derived from a Major Histocompatibility Complex Class I Antigen Is Required to Affect Insulin Receptor Function," *The Journal of Biological Chemistry*, 266(20):12844–12847 (1991).
Rajagopalan et al., "Chimeric Receptors Expressing Juxtamembrane Sequences of the Insulin Receptor Undergo Rapid Endocytosis in the Absence of Receptor Tyrosine Kinase Activity," *Biochemical and Biophysical Research Communications*, 211(3):714–718 (1995).
Levy–Toledan et al., "Deletion of C–terminal 113 Amino Acids Impairs Processing and Internalization of Human Insulin Receptor: Comparison of Receptors Expressed in CHO and NIH–3T3 Cells," *Biochimica et Biophysica Acta*, 1220:1–14 (1993).
Staubs et al., "Localization of the Insulin Receptor Binding Sites For the SH2 Domain Proteins p85, Syp, and GAP," *The Journal of Biological Chemistry*, 269(44):27186–27192 (1994).
Stagsted et al., "Regulation of Insulin Receptor Functions by a Peptide Derived from a Major Histocompatibility Complex Class I Antigen," *Cell*, 62:297–307 (1990).
Renfrew Haft et al., "Involvement of Dileucine Motifs in the Internalization and Degradation of the Insulin Receptor," *Journal of Biological Chemistry*, 289(42)26286–26294 (Oct. 1994).
Hamer, "Dual Role of a Dileucine Motif in Insulin Receptor Endocytosis," *Journal of Biological Chemistry*, 272(35)21685–21691 (Aug. 1997).

* cited by examiner

*Primary Examiner*—Christina Y. Chan
*Assistant Examiner*—Marianne DiBrino
(74) *Attorney, Agent, or Firm*—Bertram I. Rowland

(57) ABSTRACT

Oligopeptides having an amino acid sequence corresponding to a receptor's extracellular domain, and having sequence similarity to regulatory peptides from MHC class I antigens, enhance or replace the physiological response of ligand binding to the corresponding receptor. The oligopeptides are used in diagnosis and therapy of diseases that involve inadequate or inappropriate receptor response as well as in the screening of drug candidates that affect surface expression of receptors. Also useful for drug screening is a modified receptor molecule, where the sequence corresponding to the regulatory peptide is modified or deleted.

12 Claims, 20 Drawing Sheets

Synergistic effect of EPO-Rp on activation of EPO-receptor
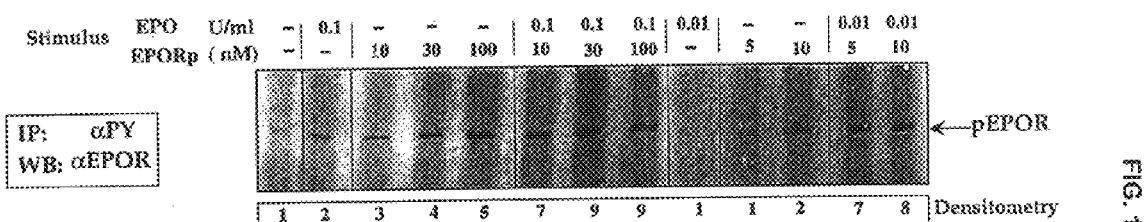
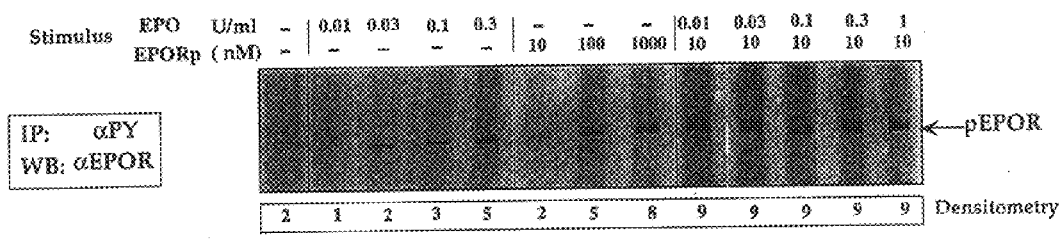
FIG. 1

EPO-Rp promotes tyrosyl phosphorylation and activation of EPO-Receptor

EPO-Rp mimics natural ligand and activates EPO-receptor

EPO-Rp - promotes EPO-Receptor dimerization
and association with JAK2

EPO-Rp selectively activates EPO-receptor
FIG. 5
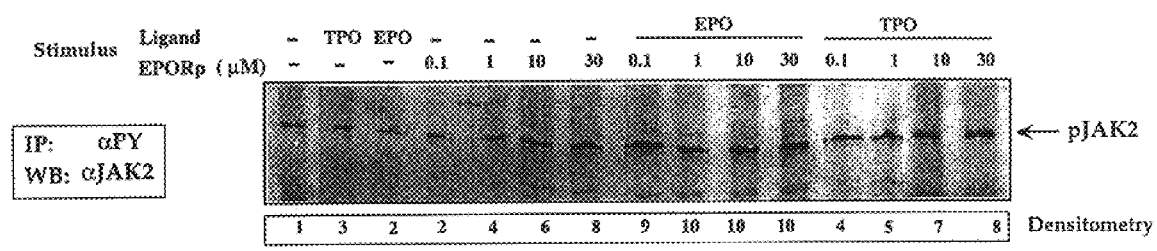
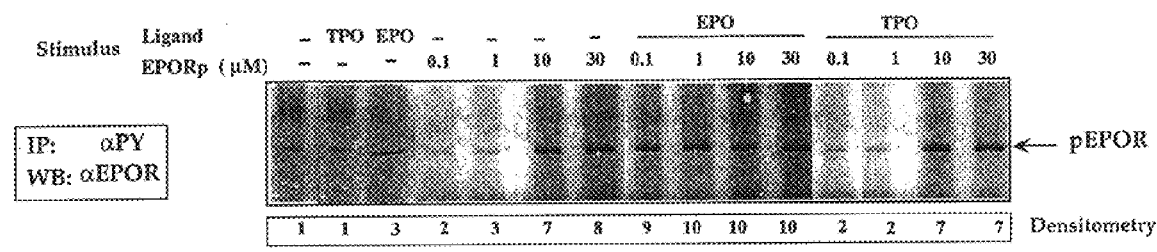

Activation (phosphorylation) of JAK2 by TPORp

Dose response

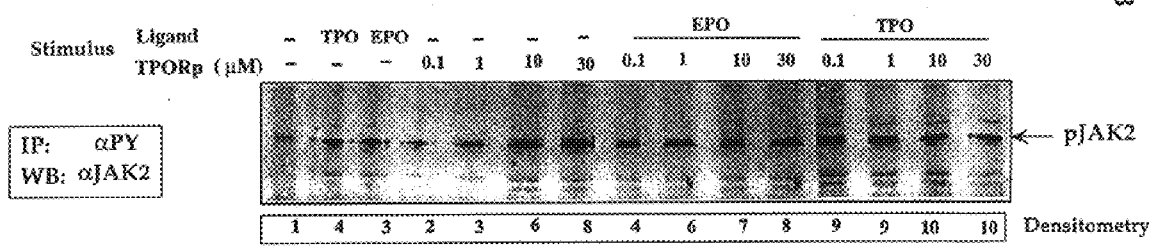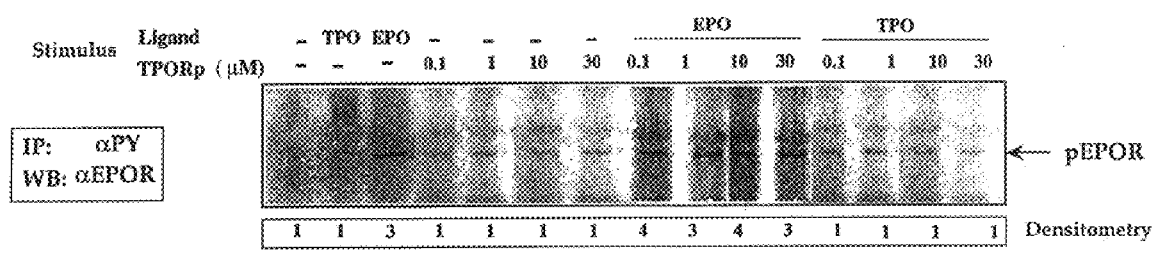
FIG. 8
TPO-Rp selectively activates TPO-receptor

TPO-Rp selectively activates TPO-receptor
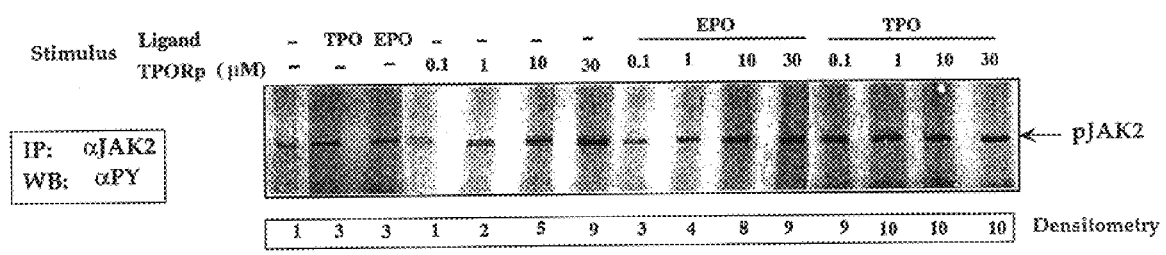
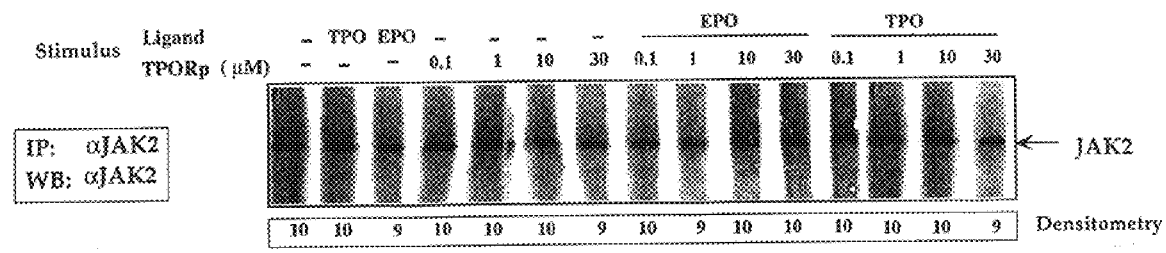
FIG. 9

FIG. 12
LRp - enhances signaling through OB-$R_L$
Activation of STAT5
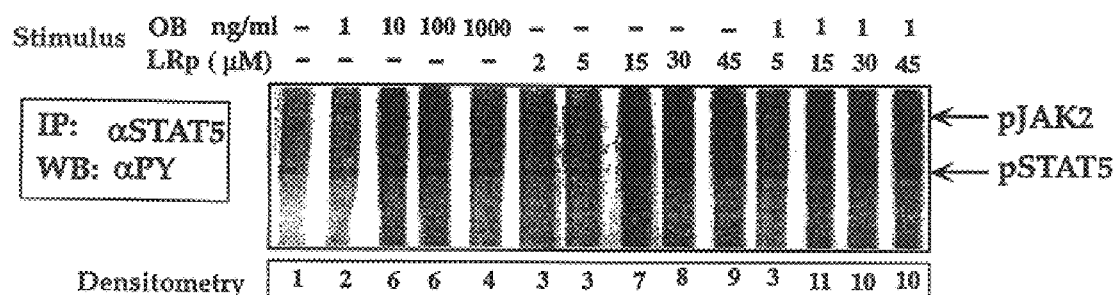
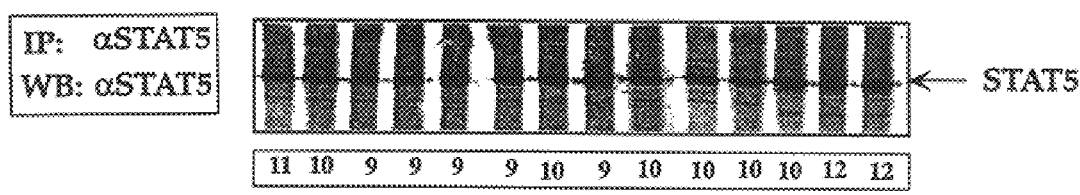

FIG. 15
GHR-peptide promotes tyrosyl phosphorylation
of JAK2
Dose response
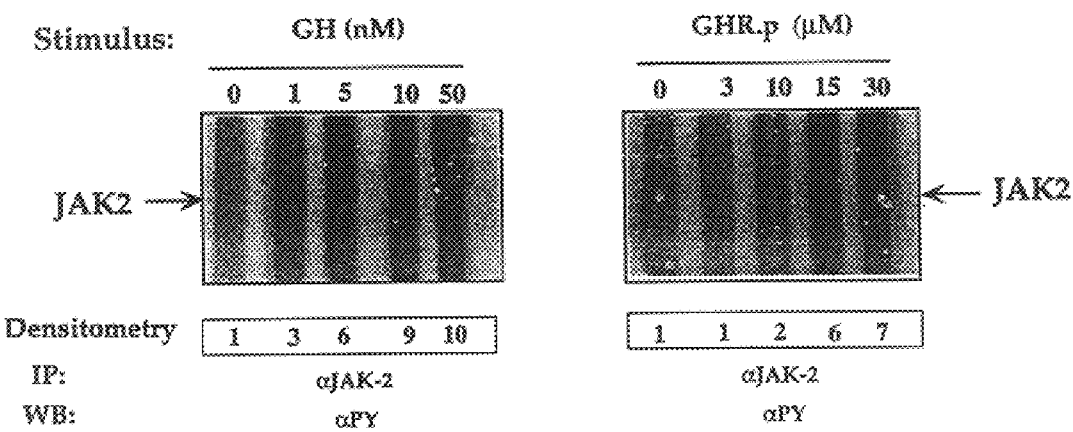
Time course
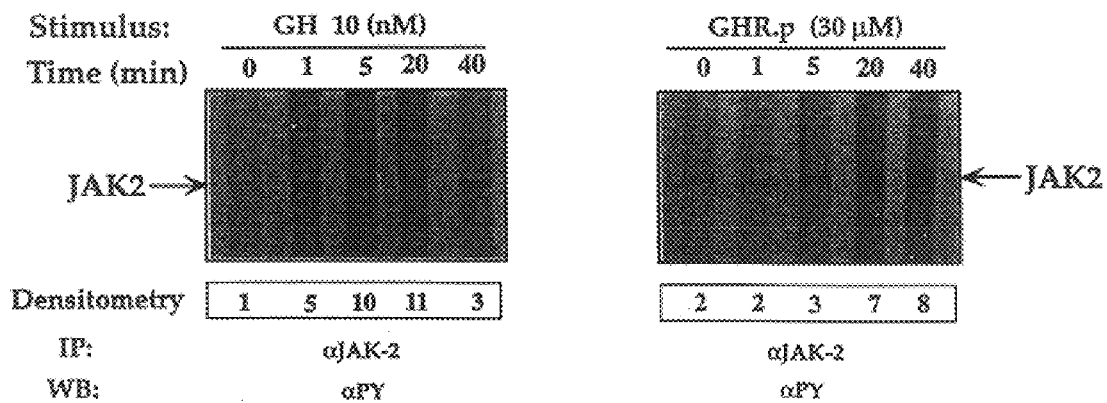

FIG. 17
Synergistic effect of GHRp on JAK2 activation
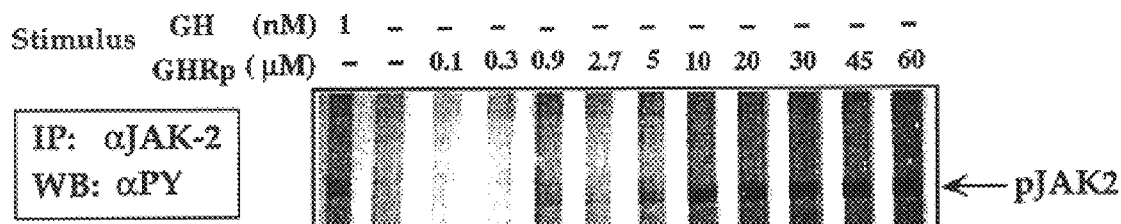
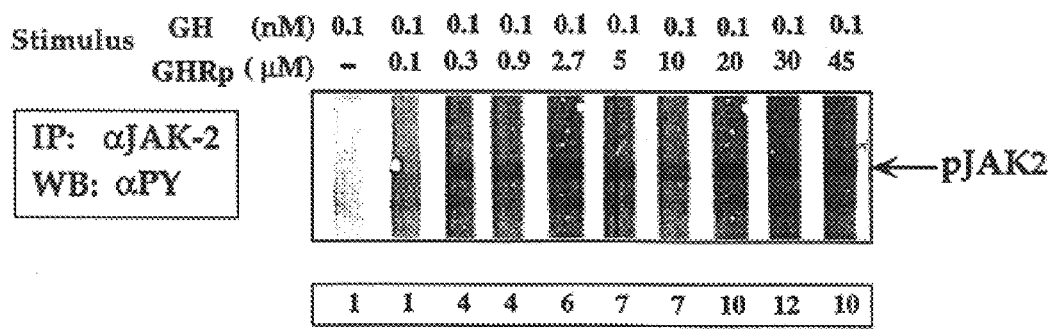

FIG. 18
GHRp - enhances signaling through GH-R
Activation of STAT5
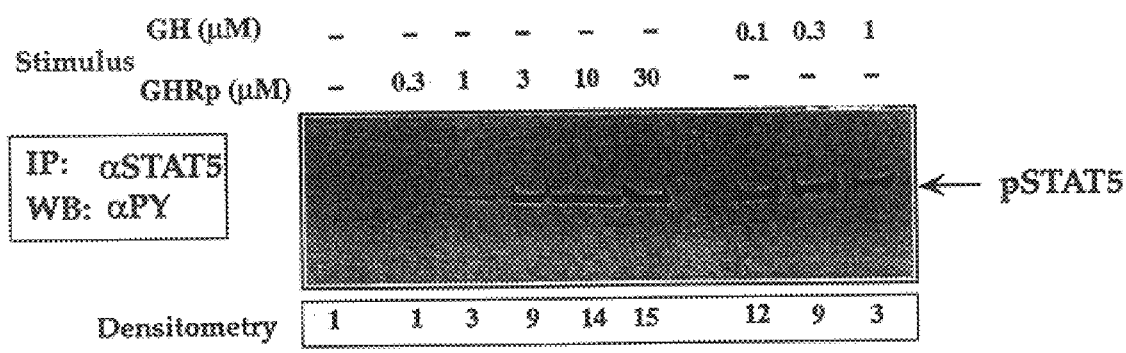
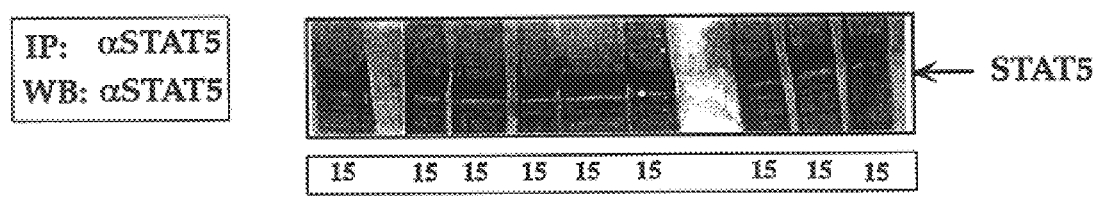

Synergistic effect of GHRp on STAT5 activation

Human Growth Hormone Receptor derived Peptide (hGH-Rp) inhibits selectively Internalization of the GH-Receptor Control peptides derived from IGF-1R and Prolactin Receptor (PL) had no effect on hGH-R, but on IGF-1R and PL-R, respectively

```
                         SEQUENCE LISTING (1) GENERAL INFORMATION:

(iii) NUMBER OF SEQUENCES: 44

(2) INFORMATION FOR SEQ ID NO:1:

(i) SEQUENCE CHARACTERISTICS:
          (A) LENGTH: 23 amino acids
          (B) TYPE: amino acid
          (C) STRANDEDNESS: unknown
          (D) TOPOLOGY: unknown (ii) MOLECULE TYPE: protein (xi) SEQUENCE DESCRIPTION: SEQ ID NO:1:

Glu Arg Glu Thr Gln Ile Ala Lys Gly Asn Glu Gln Ser Phe Arg Val
1               5                  10                  15

Asp Leu Arg Thr Leu Leu Arg
            20

(2) INFORMATION FOR SEQ ID NO:2:

(i) SEQUENCE CHARACTERISTICS:
          (A) LENGTH: 23 amino acids
          (B) TYPE: amino acid
          (C) STRANDEDNESS: unknown
          (D) TOPOLOGY: unknown (ii) MOLECULE TYPE: protein (xi) SEQUENCE DESCRIPTION: SEQ ID NO:2:

Thr Trp Leu Gly Arg Gln Gly Pro Glu Gly Pro Ser Ser Ile Pro Pro
1               5                  10                  15

Gly Thr Leu Thr Thr Leu Trp
            20

(2) INFORMATION FOR SEQ ID NO:3:

(i) SEQUENCE CHARACTERISTICS:
```

```
            (A) LENGTH: 24 amino acids
            (B) TYPE: amino acid
            (C) STRANDEDNESS: unknown
            (D) TOPOLOGY: unknown (ii) MOLECULE TYPE: protein (xi) SEQUENCE DESCRIPTION: SEQ ID NO:3:

Lys Thr Asp Ser Gln Ile Leu Lys Glu Leu Glu Glu Ser Ser Phe Arg
1               5                  10                  15

Lys Thr Phe Glu Asp Tyr Leu His
            20

(2) INFORMATION FOR SEQ ID NO:4:

(i) SEQUENCE CHARACTERISTICS:
            (A) LENGTH: 25 amino acids
            (B) TYPE: amino acid
            (C) STRANDEDNESS: unknown
            (D) TOPOLOGY: unknown (ii) MOLECULE TYPE: protein (xi) SEQUENCE DESCRIPTION: SEQ ID NO:4:

Glu Ala Glu Ala Ala Val Ala Thr Gln Glu Thr Ser Thr Val Arg Leu
1               5                  10                  15

Lys Val Ser Ser Thr Ala Val Arg Thr
            20                  25

(2) INFORMATION FOR SEQ ID NO:5:

(i) SEQUENCE CHARACTERISTICS:
            (A) LENGTH: 24 amino acids
            (B) TYPE: amino acid
            (C) STRANDEDNESS: unknown
            (D) TOPOLOGY: unknown (ii) MOLECULE TYPE: protein (xi) SEQUENCE DESCRIPTION: SEQ ID NO:5:

Lys Thr Glu Ala Glu Lys Gln Ala Glu Lys Glu Glu Ala Glu Tyr Arg
1               5                  10                  15

Lys Val Phe Glu Asn Phe Leu His
            20

(2) INFORMATION FOR SEQ ID NO:6:

(i) SEQUENCE CHARACTERISTICS:
            (A) LENGTH: 23 amino acids
            (B) TYPE: amino acid
            (C) STRANDEDNESS: unknown
            (D) TOPOLOGY: unknown (ii) MOLECULE TYPE: protein (xi) SEQUENCE DESCRIPTION: SEQ ID NO:6:

Lys Lys Glu Asn Lys Ile Val Pro Ser Lys Glu Ile Val Trp Trp Met
1               5                  10                  15

Asn Leu Ala Glu Lys Ile Pro
            20

(2) INFORMATION FOR SEQ ID NO:7:

(i) SEQUENCE CHARACTERISTICS:
            (A) LENGTH: 25 amino acids
            (B) TYPE: amino acid
            (C) STRANDEDNESS: unknown
```

(D) TOPOLOGY: unknown (ii) MOLECULE TYPE: protein (xi) SEQUENCE DESCRIPTION: SEQ ID NO:7:

Glu Lys Lys Pro Val Pro Trp Glu Ser His Asn Ser Ser Glu Thr Cys
1               5                  10                  15
Gly Leu Pro Thr Leu Val Gln Thr Tyr
            20                  25

(2) INFORMATION FOR SEQ ID NO:8:

(i) SEQUENCE CHARACTERISTICS:
        (A) LENGTH: 23 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:8:

Gly Pro His Cys Val Lys Thr Cys Pro Ala Gly Val Met Gly Glu Asn
1               5                  10                  15
Asn Thr Leu Val Trp Lys Tyr
            20

(2) INFORMATION FOR SEQ ID NO:9:

(i) SEQUENCE CHARACTERISTICS:
        (A) LENGTH: 28 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:9:

Glu Tyr Glu Leu Gln Tyr Lys Glu Val Asn Glu Thr Lys Trp Lys Met
1               5                  10                  15
Met Asp Pro Ile Leu Thr Thr Ser Val Pro Val Tyr
            20                  25

(2) INFORMATION FOR SEQ ID NO:10:

(i) SEQUENCE CHARACTERISTICS:
        (A) LENGTH: 23 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:10:

Ala Arg Gly Gly Thr Leu Glu Leu Arg Pro Arg Ser Arg Tyr Arg Leu
1               5                  10                  15
Gln Leu Arg Ala Arg Leu Asn
            20

(2) INFORMATION FOR SEQ ID NO:11:

(i) SEQUENCE CHARACTERISTICS:
        (A) LENGTH: 23 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:11:

Gln Arg Val Glu Ile Leu Glu Gly Arg Thr Glu Cys Val Leu Ser Asn
1               5                   10                  15

Leu Arg Gly Arg Thr Arg Tyr
            20

(2) INFORMATION FOR SEQ ID NO:12:

(i) SEQUENCE CHARACTERISTICS:
        (A) LENGTH: 24 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:12:

Glu Met Gln Ser Pro Met Gln Pro Val Asp Gln Ala Ser Leu Pro Gly
1               5                   10                  15

His Cys Arg Glu Pro Pro Pro Trp
            20

(2) INFORMATION FOR SEQ ID NO:13:

(i) SEQUENCE CHARACTERISTICS:
        (A) LENGTH: 21 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:13:

Asp Pro Asp Glu Gly Val Ala Gly Ala Pro Thr Gly Ser Ser Pro Gln
1               5                   10                  15

Pro Leu Gln Pro Leu
            20

(2) INFORMATION FOR SEQ ID NO:14:

(i) SEQUENCE CHARACTERISTICS:
        (A) LENGTH: 22 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:14:

Gln Glu Glu Gly Ala Asn Thr Arg Ala Trp Arg Thr Ser Leu Leu Ile
1               5                   10                  15

Ala Leu Gly Thr Leu Leu
            20

(2) INFORMATION FOR SEQ ID NO:15:

(i) SEQUENCE CHARACTERISTICS:
        (A) LENGTH: 28 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:15:

```
Glu Pro Ser Leu Arg Ile Ala Ala Ser Thr Leu Lys Ser Gln Ile Ser
1               5                   10                  15

Tyr Arg Ala Arg Val Arg Ala Trp Ala Gln Cys Tyr
                20                  25
```

(2) INFORMATION FOR SEQ ID NO:16:

(i) SEQUENCE CHARACTERISTICS:
        (A) LENGTH: 28 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:16:

```
Asp Tyr Glu Thr Arg Ile Thr Glu Ser Lys Cys Val Thr Ile Leu His
1               5                   10                  15

Lys Gly Phe Ser Ala Ser Val Arg Thr Ile Leu Gln
                20                  25
```

(2) INFORMATION FOR SEQ ID NO:17:

(i) SEQUENCE CHARACTERISTICS:
        (A) LENGTH: 20 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:17:

```
Pro Ala Gln Glu Val Ala Arg Gly Val Leu Thr Ser Leu Pro Gly Asp
1               5                   10                  15

Ser Val Thr Leu
                20
```

(2) INFORMATION FOR SEQ ID NO:18:

(i) SEQUENCE CHARACTERISTICS:
        (A) LENGTH: 26 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:18:

```
Gly Lys Ser Asn Ile Cys Val Lys Val Gly Glu Lys Ser Leu Thr Cys
1               5                   10                  15

Lys Lys Ile Asp Leu Thr Thr Ile Val Lys
                20                  25
```

(2) INFORMATION FOR SEQ ID NO:19:

(i) SEQUENCE CHARACTERISTICS:
        (A) LENGTH: 21 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:19:

```
Glu Asp Met Gly Asn Asn Thr Ala Asn Trp Arg Met Leu Leu Arg Ile
1               5                   10                  15
```

```
Leu Pro Gln Ser Phe
            20

(2) INFORMATION FOR SEQ ID NO:20:

(i) SEQUENCE CHARACTERISTICS:
        (A) LENGTH: 21 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:20:

Glu Val Leu Gly Asn Asp Thr Ala Lys Trp Arg Met Val Leu Arg Ile
1               5                   10                  15
Leu Pro His Thr Phe
            20

(2) INFORMATION FOR SEQ ID NO:21:

(i) SEQUENCE CHARACTERISTICS:
        (A) LENGTH: 19 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:21:

Glu Leu Asp Pro Gly Phe Ile His Glu Ala Arg Leu Arg Val Gln Met
1               5                   10                  15
Ala Thr Leu (2) INFORMATION FOR SEQ ID NO:22:

(i) SEQUENCE CHARACTERISTICS:
        (A) LENGTH: 22 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:22:

Glu Val Ile Thr Asp Ala Val Ala Gly Leu Pro His Ala Val Arg Val
1               5                   10                  15
Ser Ala Arg Asp Phe Leu
            20

(2) INFORMATION FOR SEQ ID NO:23:

(i) SEQUENCE CHARACTERISTICS:
        (A) LENGTH: 30 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:23:

Glu Gln Pro Thr Gln Leu Glu Leu Pro Glu Gly Cys Gln Gly Leu Ala
1               5                   10                  15
Pro Gly Thr Glu Val Thr Tyr Arg Leu Gln Leu His Met Leu
            20                  25                  30
```

(2) INFORMATION FOR SEQ ID NO:24:

(i) SEQUENCE CHARACTERISTICS:
        (A) LENGTH: 22 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:24:

Glu Trp Ser Asp Lys Gln Cys Trp Glu Gly Glu Asp Leu Ser Lys Lys
1               5                   10                  15

Thr Leu Leu Arg Phe Trp
            20

(2) INFORMATION FOR SEQ ID NO:25:

(i) SEQUENCE CHARACTERISTICS:
        (A) LENGTH: 22 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:25:

Lys Gln Asp Lys Lys Ile Ala Pro Glu Thr Arg Arg Ser Ile Glu Val
1               5                   10                  15

Pro Leu Asn Glu Arg Ile
            20

(2) INFORMATION FOR SEQ ID NO:26:

(i) SEQUENCE CHARACTERISTICS:
        (A) LENGTH: 34 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:26:

Asp Pro Asn Ile Thr Val Glu Thr Leu Glu Ala His Gln Leu Arg Val
1               5                   10                  15

Ser Phe Thr Leu Trp Asn Glu Ser Thr His Tyr Gln Ile Leu Leu Thr
            20                  25                  30

Ser Phe (2) INFORMATION FOR SEQ ID NO:27:

(i) SEQUENCE CHARACTERISTICS:
        (A) LENGTH: 21 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:27:

Glu Ile Thr Thr Asp Val Glu Lys Ile Gln Glu Ile Arg Tyr Arg Ser
1               5                   10                  15

Lys Leu Lys Leu Ile
            20

(2) INFORMATION FOR SEQ ID NO:28:

```
    (i) SEQUENCE CHARACTERISTICS:
        (A) LENGTH: 22 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:28:

Glu Ala Arg Cys Asp Phe Cys Ser Asn Asn Glu Glu Ser Phe Ile Leu
1               5                   10                  15

Asp Ala Asp Ser Asn Met
            20

(2) INFORMATION FOR SEQ ID NO:29:

(i) SEQUENCE CHARACTERISTICS:
        (A) LENGTH: 22 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:29:

Thr Trp Gln Thr Pro Ser Thr Trp Pro Asp Pro Glu Ser Phe Pro Leu
1               5                   10                  15

Lys Phe Phe Leu Arg Tyr
            20

(2) INFORMATION FOR SEQ ID NO:30:

(i) SEQUENCE CHARACTERISTICS:
        (A) LENGTH: 22 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:30:

Asp Ser Gln Thr Asn Val Ser Gln Ser Lys Asp Ser Asp Val Tyr Ile
1               5                   10                  15

Thr Asp Lys Thr Val Leu
            20

(2) INFORMATION FOR SEQ ID NO:31:

(i) SEQUENCE CHARACTERISTICS:
        (A) LENGTH: 24 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:31:

Glu Trp Thr Gln Asp Arg Ala Lys Pro Val Thr Gln Ile Val Ser Ala
1               5                   10                  15

Glu Ala Trp Gly Arg Ala Asp Cys
            20

(2) INFORMATION FOR SEQ ID NO:32:

(i) SEQUENCE CHARACTERISTICS:
        (A) LENGTH: 36 amino acids
```

```
            (B) TYPE: amino acid
            (C) STRANDEDNESS: unknown
            (D) TOPOLOGY: unknown (ii) MOLECULE TYPE: protein (xi) SEQUENCE DESCRIPTION: SEQ ID NO:32:

Ser Gln Glu Gly Asn Thr Met Lys Thr Asn Asp Thr Tyr Met Lys Phe
1               5                   10                  15

Ser Trp Leu Thr Val Pro Glu Glu Ser Leu Asp Lys Glu His Arg Cys
            20                  25                  30

Ile Val Arg His
            35

(2) INFORMATION FOR SEQ ID NO:33:

(i) SEQUENCE CHARACTERISTICS:
            (A) LENGTH: 20 amino acids
            (B) TYPE: amino acid
            (C) STRANDEDNESS: unknown
            (D) TOPOLOGY: unknown (ii) MOLECULE TYPE: protein (xi) SEQUENCE DESCRIPTION: SEQ ID NO:33:

Val His Thr Glu Lys Val Asn Met Met Ser Leu Thr Val Leu Gly Leu
1               5                   10                  15

Arg Met Leu Phe
            20

(2) INFORMATION FOR SEQ ID NO:34:

(i) SEQUENCE CHARACTERISTICS:
            (A) LENGTH: 26 amino acids
            (B) TYPE: amino acid
            (C) STRANDEDNESS: unknown
            (D) TOPOLOGY: unknown (ii) MOLECULE TYPE: protein (xi) SEQUENCE DESCRIPTION: SEQ ID NO:34:

Glu Lys Thr Asp Arg Phe Val Met Lys Lys Leu Asn Asp Arg Val Met
1               5                   10                  15

Arg Val Glu Tyr His Phe Leu Ser Pro Tyr
            20                  25

(2) INFORMATION FOR SEQ ID NO:35:

(i) SEQUENCE CHARACTERISTICS:
            (A) LENGTH: 25 amino acids
            (B) TYPE: amino acid
            (C) STRANDEDNESS: unknown
            (D) TOPOLOGY: unknown (ii) MOLECULE TYPE: protein (xi) SEQUENCE DESCRIPTION: SEQ ID NO:35:

Glu Trp Glu Ile His Phe Ala Gly Gln Gln Thr Glu Phe Lys Ile Leu
1               5                   10                  15

Ser Leu His Pro Gly Gln Lys Tyr Leu
            20                  25

(2) INFORMATION FOR SEQ ID NO:36:

(i) SEQUENCE CHARACTERISTICS:
            (A) LENGTH: 27 amino acids
```

(B) TYPE: amino acid
            (C) STRANDEDNESS: unknown
            (D) TOPOLOGY: unknown (ii) MOLECULE TYPE: protein (xi) SEQUENCE DESCRIPTION: SEQ ID NO:36:

Pro Lys Thr Asp Ser Gln Ile Leu Lys Glu Leu Glu Glu Ser Ser Phe
1               5                   10                  15

Arg Lys Thr Phe Glu Asp Tyr Leu His Asn Val
            20                  25

(2) INFORMATION FOR SEQ ID NO:37:

(i) SEQUENCE CHARACTERISTICS:
            (A) LENGTH: 36 amino acids
            (B) TYPE: amino acid
            (C) STRANDEDNESS: unknown
            (D) TOPOLOGY: unknown (ii) MOLECULE TYPE: protein (xi) SEQUENCE DESCRIPTION: SEQ ID NO:37:

Gly Asn Glu Gln Ser Phe Arg Val Asp Leu Arg Thr Leu Leu Arg Tyr
1               5                   10                  15

Ala Gly Gly Gly Asn Glu Gln Ser Phe Arg Val Asp Leu Arg Thr Leu
            20                  25                  30

Leu Arg Tyr Ala
        35

(2) INFORMATION FOR SEQ ID NO:38:

(i) SEQUENCE CHARACTERISTICS:
            (A) LENGTH: 25 amino acids
            (B) TYPE: amino acid
            (C) STRANDEDNESS: unknown
            (D) TOPOLOGY: unknown (ii) MOLECULE TYPE: protein (xi) SEQUENCE DESCRIPTION: SEQ ID NO:38:

Ala Arg Arg Lys Ala Lys Ala Glu Arg Lys Leu Arg Leu Arg Pro Ser
1               5                   10                  15

Asp Leu Arg Ser Phe Leu Thr Met Phe
            20                  25

(2) INFORMATION FOR SEQ ID NO:39:

(i) SEQUENCE CHARACTERISTICS:
            (A) LENGTH: 27 amino acids
            (B) TYPE: amino acid
            (C) STRANDEDNESS: unknown
            (D) TOPOLOGY: unknown (ii) MOLECULE TYPE: protein (xi) SEQUENCE DESCRIPTION: SEQ ID NO:39:

Lys Leu Arg Thr Gln Glu Thr Arg Gly Asn Glu Val Ser His Tyr Lys
1               5                   10                  15

Arg Leu Ala Arg Ser Thr Leu Leu Leu Ile Pro
            20                  25

(2) INFORMATION FOR SEQ ID NO:40:

(i) SEQUENCE CHARACTERISTICS:
            (A) LENGTH: 25 amino acids (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:40:

Gly Lys Tyr Val Cys Leu Glu Asp Phe Pro Glu Asp Lys Arg Phe Leu
1               5                   10                  15

Ser Tyr Thr Thr Leu Leu Phe Ile Leu
            20                  25

(2) INFORMATION FOR SEQ ID NO:41:

(i) SEQUENCE CHARACTERISTICS:
        (A) LENGTH: 11 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:41:

Ser Phe Arg Val Asp Ser Glu Phe Arg Tyr Thr
1               5                   10

(2) INFORMATION FOR SEQ ID NO:42:

(i) SEQUENCE CHARACTERISTICS:
        (A) LENGTH: 25 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:42:

Cys Leu Asn Pro Met Leu Tyr Thr Phe Ala Gly Val Lys Phe Arg Ser
1               5                   10                  15

Asp Leu Ser Arg Leu Leu Thr Lys Leu
            20                  25

(2) INFORMATION FOR SEQ ID NO:43:

(i) SEQUENCE CHARACTERISTICS:
        (A) LENGTH: 25 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:43:

Cys Leu Asn Pro Met Leu Tyr Thr Phe Ala Gly Val Lys Arg Phe Ser
1               5                   10                  15

Asp Leu Ser Arg Leu Leu Thr Lys Leu
            20                  25

(2) INFORMATION FOR SEQ ID NO:44:

(i) SEQUENCE CHARACTERISTICS:
        (A) LENGTH: 25 amino acids
        (B) TYPE: amino acid
        (C) STRANDEDNESS: unknown
        (D) TOPOLOGY: unknown (ii) MOLECULE TYPE: protein -continued (xi) SEQUENCE DESCRIPTION: SEQ ID NO:44:

```
Cys Leu Asn Pro Met Leu Tyr Thr Phe Ala Gly Val Lys Arg Phe Ser
1               5                   10                  15

Asp Leu Ser Arg Leu Leu Thr Lys Leu
            20                  25
```

RECEPTOR DERIVED PEPTIDES AS MODULATORS OF RECEPTOR ACTIVITY

This application is a continuation-in-part application of U.S. Ser. No. 08/788,820, filed Jan. 23, 1997, which is a continuing application of U.S. Ser. No. 08/701,382, filed Aug. 22, 1996, now U.S. Pat. No. 6,004,758, which is a continuing application of U.S. Ser. No. 08/612,999, filed Mar. 8, 1996, now U.S. Pat. No. 5,952,293.

INTRODUCTION

1. Technical Field

The field of this invention is the modulation of activity of cell surface receptors, including both modulation of internalization of the receptor and modulation of activation of the receptors in the presence or absence of ligand.

2. Background

The complex regulatory balance between hormones, receptors and responding cells is critical to the correct functioning of multicellular organisms. Subtle environmental and genetic factors can disrupt this balance, sometimes resulting in disease. The advent of molecular biology has meant that medically important hormones can be made available in therapeutically useful amounts. Among them are human growth hormone, EPO, TPO, insulin-like growth factor, insulin, epidermal growth factor, and numerous others.

A condition of great economic and medical significance is insulin resistance, which is an essential feature of a great variety of clinical disorders, such as diabetes mellitus, obesity and certain types of hypertension. Individuals with non-insulin dependent diabetes present with insulin resistance in peripheral tissues. They have a subnormal glucose utilization in skeletal muscle, where glucose transport across the cell membrane of skeletal muscle is the rate limiting step in glucose metabolism. It is possible that a defect exists in insulin-dependent glucose transport in skeletal muscle in diabetic states, where decreased levels of the glucose transporter 4 protein (GLUT4) have been observed. In adipose and muscle cells, insulin stimulates a rapid and dramatic increase in glucose uptake, primarily by promoting the redistribution of the GLUT4 glucose transporter from its intracellular storage site to the plasma membrane.

Insulin resistance may also be attributed to a defect in insulin action at the cellular level. The insulin receptor is activated by binding of insulin to the alpha-subunit of the receptor, which causes autophosphorylation of the intracellular beta-subunit region. The activated insulin receptor couples to cytosolic receptor substrates that can affect signaling cascades, resulting in the pleiotropic hormone response. Most proteins involved in the signal transduction pathway are not known yet, but each of them might play a role in the various forms of insulin resistance. The heterogeneous nature of insulin resistance makes treatments that can act "upstream" of the signal transduction pathways very attractive, because a number of different pathologies could be treated with a single drug.

Specific peptides have been previously shown to enhance the cellular response to certain hormones. This effect has been attributed to inhibition of the internalization of the corresponding hormone receptors. Insulin-stimulated glucose uptake is increased by adding the peptides to responding cells, offering the possibility of improved therapy for insulin dependent and insulin resistant diabetes. The enhanced response may also be exploited in therapies involving other hormones. Improvements in the specificity of agents that enhance the activity of insulin and other hormones are of considerable interest for their therapeutic benefits. The site of action for such peptides on receptors molecules is of interest for drug evaluation and design.

In addition, there is great interest in finding ligand replacements, or mimetics, that could be used in place of the naturally-occuring ligand. This is of particular interest for ligand hormones that may have a number of biological functions of which only a subset are to be regulated.

Relevant Literature

Several groups have examined the glucose transporter and insulin receptor for residues that are involved in internalization. Rajagopalan et al. (1995) *Biochem. Biophys. Res. Commun.* 211:714–8 found that residues GPYL950–953 served as the predominant endocytosis signal and the sequence NPEY957–960 as a secondary signal. Levy-Toledano et al. (1993) *Biochem. Biophys. Acta.* 1220:1–14 suggest that the structural domain located 43–113 amino acids from the C-terminus is required in intact cells for insulin-stimulated autophosphorylation and signal transmission. Verhey et al. (1995) *J. Cell Biol.* 130:1071–9 identified sequences involved in the differential subcellular localization and hormone-responsiveness of glucose transporter isoforms. The COOH-terminal 30 amino acids of GLUT4 are sufficient for its correct localization to an intracellular storage pool that translocates to the cell surface in response to insulin. In addition, there is a report of important leucine residues in insulin receptor endocytosis. See Hamer et al., J. Biol. Chem. 272:21685 (1997).

U.S. Pat. No. 5,385,888, issued Jan. 31, 1995, describes Class I MHC peptide modulation of surface receptor activity. Data presented in International patent application PCT/US94/09189 suggest that these peptides must be in an ordered conformation to be biologically active. The composition and uses of such peptides are further described in International application PCT/US93/01758. The peptides are further disclosed in International application PCT/US89/00876.

Regulation of receptor internalization by the major histocompatibility complex class I molecule is shown by Olsson et al. (1994) *Proc. Natl. Acad. Sci.* 91:9086–90, and by a peptide derived from the insulin receptor in Naranda et al., *Proc. Natl. Acad. Sci.* 94:11692 (1997). Peptides derived from the alpha 1 domain of the major histocompatibility complex class I protein (MHC-I) inhibit internalization of some receptors, thereby increasing the steady-state number of active receptors on the cell surface. It is suggested that MHC-I participates in the regulation of cell surface receptor activity. Stagsted et al. (1993) *J. Biol. Chem.* 268:22809–13 demonstrate that such peptides inhibit the internalization of glucose transporters (GLUT4) and insulin-like growth factor II (IGF-II) receptors in insulin-stimulated cells.

SUMMARY OF THE INVENTION

It is an object of the invention to provide compositions and methods useful in the modulation of receptor activity. Accordingly, the present invention provides oligopeptides comprising at least about 8 amino acids and less than about 40 amino acids which has an amino acid sequence corresponding to the activation sequence of the extracellular domain of a cell surface receptor. Also provided are oligopeptides at least about 90% homologous to an activation sequence of a cell-surface receptor.

In an additional aspect, the invention provides methods of modulating the internalization of a cell-surface receptor containing an activation sequence comprising binding an exogeneous compound to said activation sequence.

In a further aspect, the invention provides mammalian cells comprising a modified cell surface receptor, wherein the modification comprises an amino acid sequence substitution, insertion or deletion in an activation sequence of the region of the extracellular domain.

In an additional aspect, the invention provides methods of determining an activation sequence of a cell surface receptor comprising searching for a region of sequence similarity between the cell surface receptor and the sequence of an α1-domain of an MHC Class I antigen.

In a further aspect, the invention provides methods for screening for a bioactive agent capable of binding to the activation sequence of a cell surface receptor, comprising combining a cell surface receptor and a candidate bioactive agent, and determining the binding of the candidate agent to the activation sequence of the cell surface receptor.

In an additional aspect, the invention provides methods for screening for an bioactive agent capable of modulating the internalization of a type-1 cell-surface receptor, the method comprising the steps of adding a ligand bound by the cell surface receptor and a candidate bioactive agent to a cell comprising the cell surface receptor. The effect of the candidate bioactive agent on the internalization of the receptor is then determined.

In a further aspect, the invention provides methods for screening for an bioactive agent capable of modulating the internalization of a type-2 cell-surface receptor, the method comprising the steps of adding a candidate bioactive agent to a cell comprising the cell surface receptor. The effect of the candidate bioactive agent on the internalization of the receptor is then determined.

In an additional aspect, the invention provides compositions comprising a cell-surface receptor with an exogeneous compound bound to the activation sequence.

BRIEF DESCRIPTION OF THE DRAWINGS

FIG. 1: Synergistic effect of EPO receptor derived peptide (EPO-Rp, SEQ ID NO:11) on the effect of EPO as measured by phosphorylation of the EPO receptor (EPO-R), IP, immunoprecipitation; WB, Western Blot. FIG. 1 comprises digital images of western blots. Cells were incubated for 20 minutes with EPO and/or EPO-Rp prior to lysis and IP and WB. The panels show that EPO-Rp in itself stimulates the EO-R, but also that EPO-Rp has a strong synergistic effect as 0.0 1 U/ml alone has an effect, 10 nM EPO-Rp a weak effect, but that 0.0 U/ml EPO plus 10 nM EPO-Rp has a strong effect (FIG. 1 WB on the right). This result thus indicates that the EPO-Rp can strongly enhance the endogenous levels of EPO, e.g. in patients with kidney disease where the production of EPO is reduced significantly.

FIG. 2 is a digital image of a western blot. Doses for the two compounds were chosen to give a strong signal on their own. The EPO-induced signal is faster than EPO-Rp (5 minutes with peak at 15 minutes versus 15 minutes and with a duration of at least 90 minutes for EPO-Rp). Thus, the duration of the effect of EPO-Rp is much longer than that of EPO.

FIG. 3 is a digital image of a western blot. Growth hormone receptor derived peptide (GHRp) was used as control in a concentration of 10 μM that strongly enhances growth hormone receptor activity. 2.5 U/ml EPO in activity corresponds to about 30–100 nM EPO-Rp.

FIG. 4 is a digital image of a western blot.

FIG. 5 depicts that EPO-Rp selectively activates EPO-Receptor. TF1 cells were stimulated for 20 min with 0.1 U/ml of EPO, 10 nM TPO, different concentrations of EPO-Rp, and combinations of TPO or EPO (at the same concentrations) together with EPO-Rp. Cells were lysed and immunoprecipitated with anti-phosphotyrosine antibody (PY). Western blot analysis was performed by using anti-EPOR antibody that specifically recognizes EPO-R and anti-JAK2 antibody that will recognize a kinase that specifically associates only with activated receptors. FIG. 5 is a digital image of western blot. EPO and EPO-R peptide acts synergistically in activating EPOR (bottom panel) and JAK2 kinase (upper panel). TPO together with EPO-R peptide does not enhance the signal; activation of JAK2 with TPO and EPORp is additive (top panel), because TPO activates its own receptor that also associates with JAK2. As well, bottom panel shows that TPO with EPORp does not activate the EPOR, as the signal is due to presence of the peptide only.

FIG. 8 shows that TPORp selectively activates TPO-Receptor. Cells were stimulated for 20 min with 0.1 U/ml of EPO, 10 nM TPO, different concentrations of TPOR-peptide, and combinations of TPO or EPO (at the same concentrations) together with TPO-R peptide. Cells were lysed and immunoprecipitated with anti-PY antibody. Western blot analysis was performed by using anti-EPOR antibody that specifically associates only with activated receptors (EPOR or TPOR). Figure is a digital image of western blot. TPO and TPO-R peptide act synergistically in activating JAK2 kinase through the TPO-R (upper panel). EPO together with TPO-R peptide does not enhance the signal in the same way as activation of JAK2 with EPO and TPORp as additive. In addition, EPO with TPORp does not activate the EPOR, as the signal seen on the bottom panel is due to presence of the EPO only.

FIG. 9 demonstrates that TPORp activates JAK2 kinase through TPO-Receptor. Experiment was performed as on FIG. 8, except that cells were IP with anti-JAK2 antibody. WB probed with anti-PY antibody (top panel) shows that TPORp activates JAK2 kinase in two ways: mimicking TPO activation and acting synergistically with TPO. WB and anti-JAK2 antibody (bottom panel) shows that all immunoprecipitates contained the same amount of JAK2 protein.

Numbers in the box below the panel show quantification of western blots. For that purpose, the membranes were scanned and intensity of the protein bands was quantitated using the NIH 1.5 Image program. Upper values are corresponding to JAK2 protein, lower to STAT5.

Figure 2:
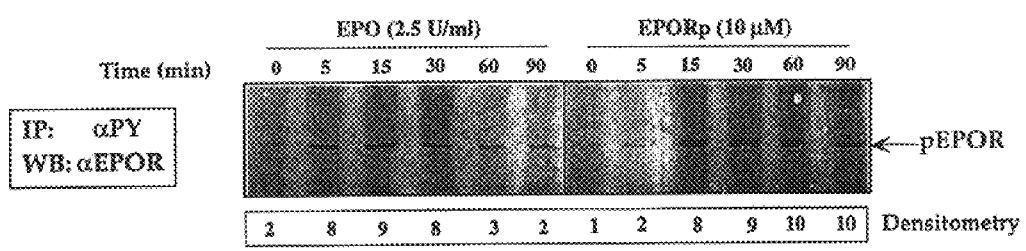
FIG. 2: Kinetics for the effect of EPO and the EPO receptor derived peptide (EPO-Rp, SEQ ID NO:11).
Figure 3:
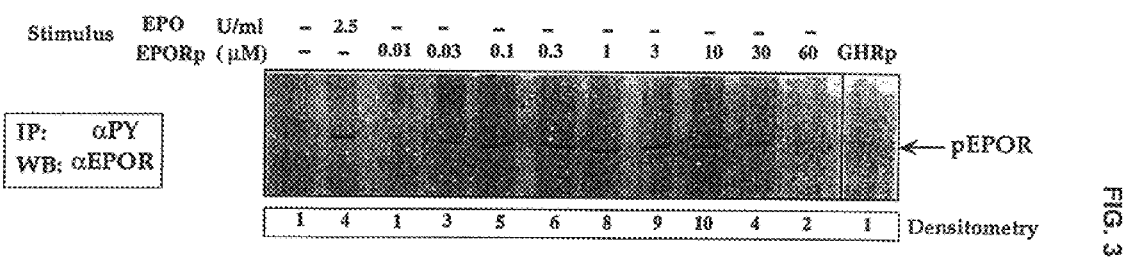
FIG. 3: Demonstration of the stimulation of EPO-R with EPO-Rp. The cells were stimulated for 20 minutes.
Figure 4:
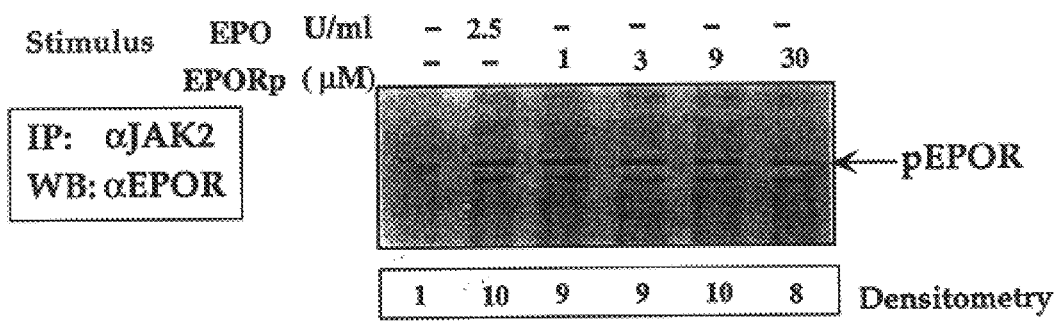
FIG. 4: Dimerization of EPO-R is assumed to induce intracellular association between JAK2 and EPO-R. Using an antibody to JAK2 as precipitating antibody, both EPO and EPO-Rp results in association of EPO-R with JAK2.
Figure 6:
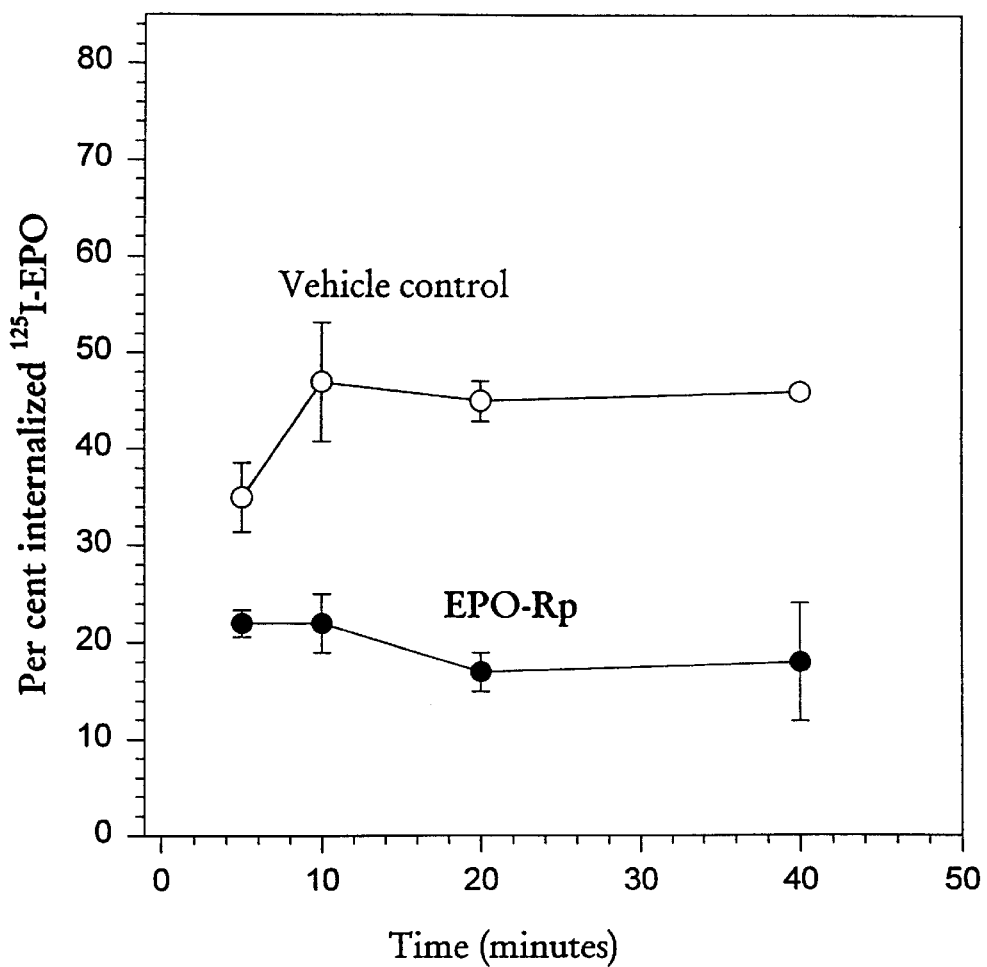
FIG. 6 depicts the inhibition of EPO-R internalization with EPO-Rp. Internalization of [$^{125}$] EPO was measured in TF1 cells in the presence or absence of EPORp. Cells were preincubated for 30 min at 37° C., followed by addition of [$^{125}$]-EPO and 15 μM peptide concentration (EPORp). Cells were further incubated at 37° C. for different times and internalized ligand was measured by the method of acid wash. Cells were spun through oil mixture to separate bound from unbound ligand. Internalized ligand is calculated as percent of [$^{125}$]-EPO resistant to acid wash (intracellular) versus the total mount of hormone bound to the cells. Thus, EPORp inhibits internalization of EPO-Receptor and therefore extends its cell surface time.
Figure 7:
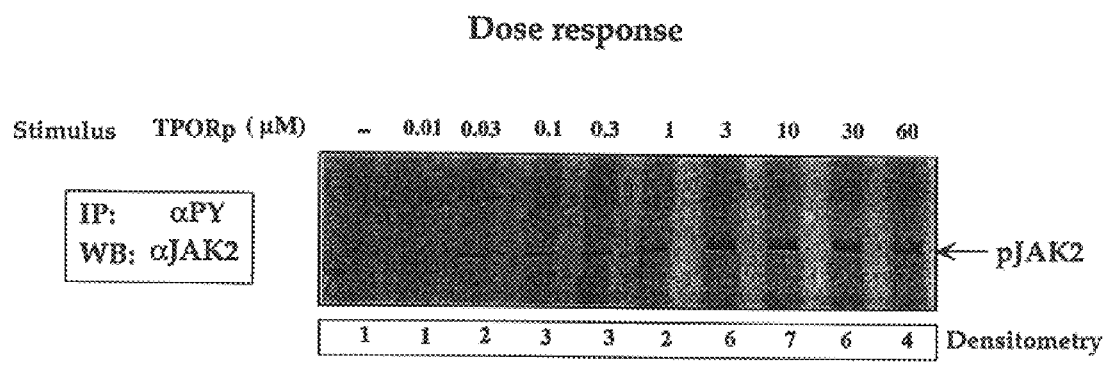
FIG. 7 demonstrates the activation (phosphorylation) of JAK2 kinase by TPO receptor derived peptide (TPO-Rp; SEQ ID NO:10). Different concentrations of peptide (as indicated) were added to cells for 20 min and IP with anti-PY antibody was performed, followed by western blot using anti-JAK2 antibody. This kinase will get activated only if it can bind to dimerized (biologically active) TPO-Receptors. Thus, TPORp enhances signaling through TPO-Receptor.
Figure 10:
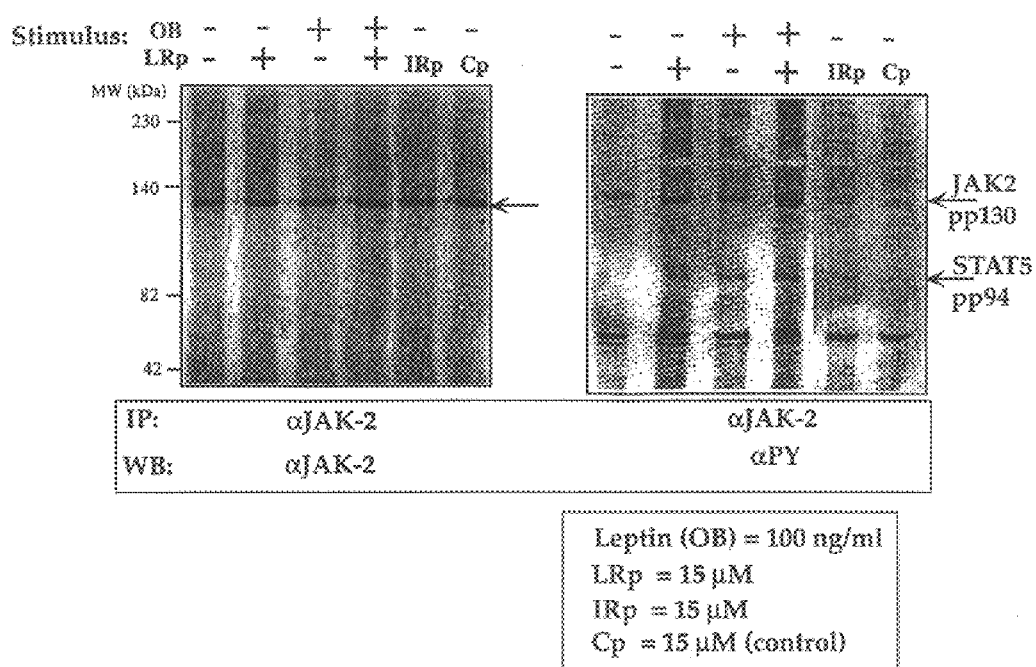
FIG. 10 depicts the activation of Leptin Receptor (OB-R) signaling with Leptin Receptor derived peptide (LRp). COS-1 cells were transiently transfected with long form of Leptin Receptor (OB-$R_1$) and stimulated for 20 min with 6 nM Leptin, 15 μM LRp or combination thereof. Expression of Leptin Receptor was confirmed by western blot analysis using specific anti-OBR antibody and by binding of $[^{125}I]$-Leptin to the transfected cells. Cells were lysed and immunoprecipitation was performed with anti-JAK2 antibody. WB with the same antibody (left panel) shows that equal amount of proteins are present in all the immunoprecipitates. WB with anti-PY antibody (right panel) demonstrates that LRp activates JAK2 through Lepin Receptor, because there is identical enhancement of protein phosphorylation signal in both cases; cells stimulated with Leptin or LRp. As indicated on the figure upper band represents phosphorylated JAK2 molecule, middle band represents phosphorylated STAT5 molecule (both specific proteins in a signaling pathway of OB-R), and bottom band is an unidentified protein whose phosphorylation does not change between non-stimulated and stimulated cells. Two additional peptides were used as a control of specificity: Insulin receptor derived peptide (IRp; SEQ ID NO:3) a peptide that at 15 μM concentration strongly activates signaling through the Insulin receptor, and Cp, a peptide derivative of Leptin Receptor as well, but without any similarity to MHC-I peptide. None of these peptides activated JAK2 or STAT5 proteins.
Figure 11:
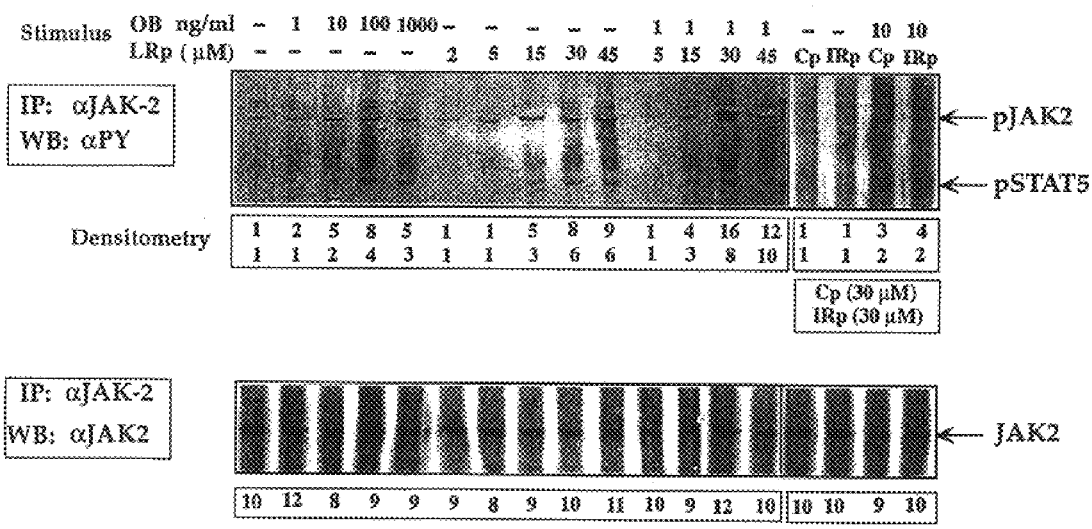
FIG. 11 demonstrates that the LRp mimics Leptin and shows a synergistic effect together with Leptin in activation of Leptin Receptor signaling. COS-1 cells were transfected with long form of Leptin receptor and stimulated for 20 min with different concentrations of Leptin (OB), LRp and the lowest dose of OB (1 ng/ml) together with different peptide concentrations, as indicated on the figure. IP was performed with anti-JAK2 antibody. Bottom panel WB shows that all the immunoprecipitates contain the same amount of JAK2 protein. WB with anti-PY (upper panel) shows activation (phosphorylation) of JAK2 and STAT5 by OB and LRp. Both, natural ligand and the peptide activate JAK2 to the same extent. When combined, there is a synergistic effect between them; e.g., the activation of JAK2 is stronger when 1 ng/ml of OB and 30 μM LRp were added together (16 arbitrary units), than when the cells were stimulated with the same compounds but separately (2 and 8 units). CP and IRp showed no effect on protein phosphorylation when alone or combined with OB.

FIG. 12 shows the effect of LRp on activation of STAT5 through Leptin Receptor. STAT5 is transcription factor that specifically will bind to activated JAK2, which previously needs to be phosphorylated by interacting with dimerized receptors. Experiments were performed as described in FIG. 11, except that anti-STAT5 antibody was used instead of JAK2. WB with anti-PY antibody (upper panel) shows that LRp mimics the action of Leptin (OB) and when combined with it acts synergistically. Lower panel shows that all the immunoprecipitates contain the same amount of STAT5 protein.

Figure 13:
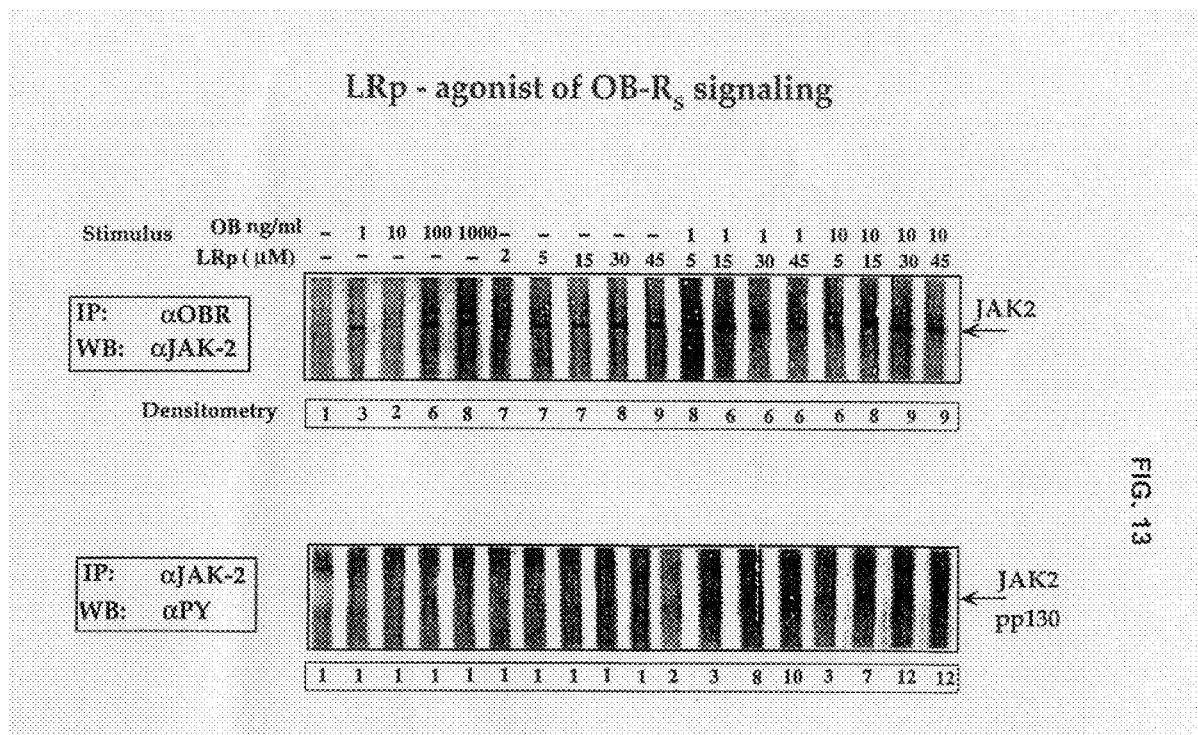

FIG. 13 demonstrates the effect of LRp on the signaling of the Leptin Receptor short form (OB-$R_s$). COS-1 cells were transfected with short form of Leptin receptor and stimulated for 20 min with different concentrations of Leptin (OB), LRp and two different doses of OB (1 ng/ml and 10 ng/ml) together with different peptide concentrations, as indicated on the figure. IP was performed with anti-OBR antibody and subsequent blot was probed with JAK2 antibody. WB on the upper panel shows that JAK2 protein associates with Leptin receptor only when the receptor has been activated. LRp shows that same effect as natural ligand. On the bottom panel, cells were IP with anti-JAK2 antibody and the membrane was probed with anti-PY. Phosphorylation (activation) of JAK2 is observed only when both LRp and Leptin are present. Thus, LRp and Leptin together can activate short form of leptin receptor (form of the receptor that is expressed in db/db animals), the effect that is not observed when only one of the compound is added.

Figure 14:
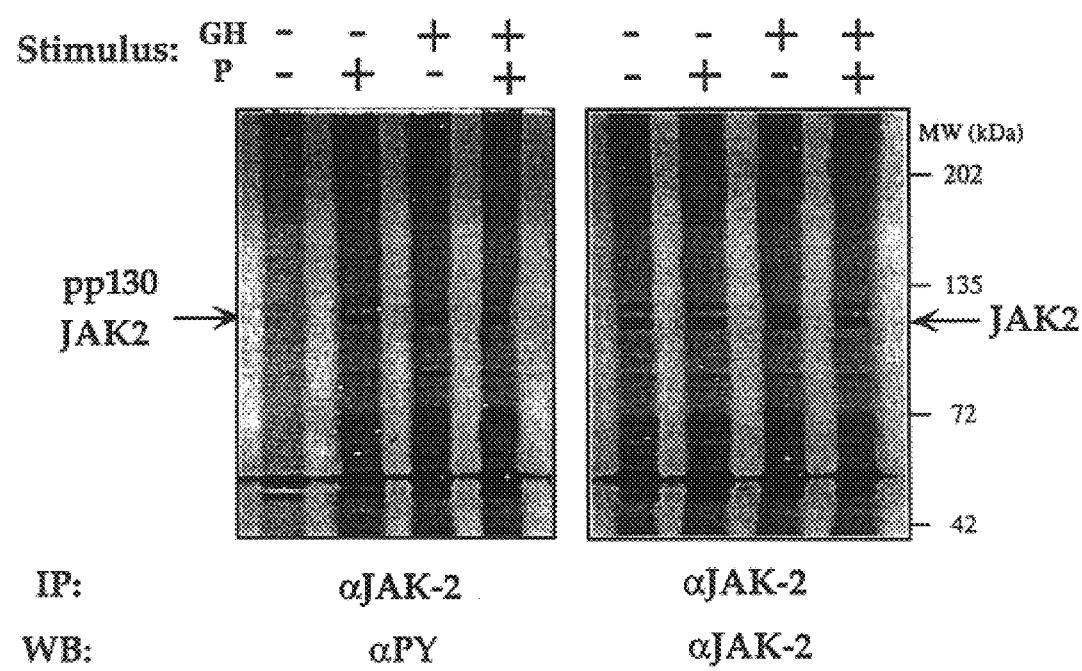

FIG. 14 demonstrates the activation of Growth Hormone Receptor (GHR) by GHR-derived peptide (GH-Rp; SEQ ID NO:9). IM9 cells were stimulated for 20 min with 10 nM GH, 30 μM GHRp and combination thereof. IP was performed with anti-JAK2 antibody. WB and JAK2 antibody (right panel) shows the same amount of the protein present in all the immunoprecipitates. WB with anti-PY demonstrate equal activation (phosphorylation) of JAK2 by GH and GHR-peptide.

FIG. 15 shows the kinetics for the effect of GH and GHRp. Doses for the two compounds are as indicated on the top of the panels. Upper panel shows that GH and GHRp phosphorylate JAK2 to the same extent; most likely by inducing dimerized conformation between GH-Receptors (receptor dimerization is assumed to induce intracellular association between JAK2 and GHR). The GH-induced signal of JAK2 phosphorylation is faster than GHRp (1 min with duration of approximately 30 min, versus 5 min and with duration of at least 40 min for GHRp). Thus, the duration of the effect of GHRp is much longer than that of GH.

Figure 16:
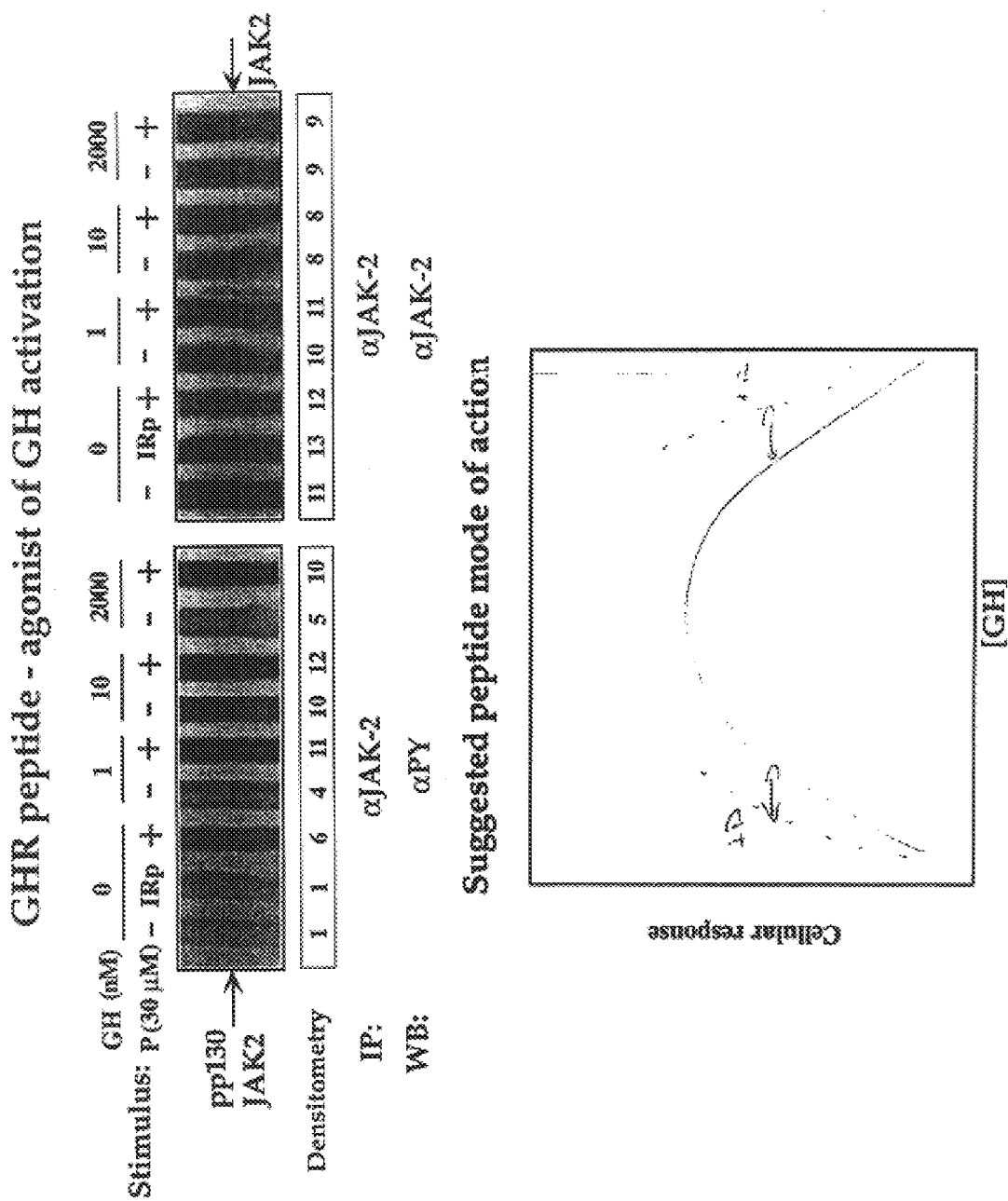

FIG. 16 demonstrates that GHRp (P) broadens the range of GH action. IM9 cells were stimulated with 1 nM, 10 nM and 2 μM GH in the presence or absence of GHRp. Those concentrations of GH were use, because it is known that GH action has the bel-shaped dose response curve with an $IC_{50}$ at 2 μM GH concentration. IP was performed with anti-JAK2; WB with the same antibody (right panel) or with anti-PY (left panel). Blot probed with anti-JAK2 shows that the same amount of protein is present in all immunoprecipitates. Anti-PY WB demonstrates that peptide enhances JAK2 activation approximately three times in the presence of 1 nM GH. In the GH inhibitory concentration of 2 μM GHRp has increased natural hormone response approximately two times. Therefore, GHRp broadens the range of GH action by increasing its activity at low concentrations and extending the activity to higher hormone concentrations.

FIG. 17 demonstrates synergistic effect of GHRp on the GH action. Cells were stimulated for 20 minutes with different concentrations of the GHR-peptide alone (top panel), or in combination with 1 nM (middle panel) and 0.1 nM GH (bottom panel).

IP was performed with anti-JAK2 and WB with anti-PY antibody. GHRp shows strong synergistic effect with both concentrations of GH; (i) no effect on JAK2 phosphorylation is observed with low (up to 5 μM) peptide concentrations, but when combined with 1 nM GH, activation of JAK2 is significantly increased (1 versus 12 arbitrary units); (ii) 0.1 nM concentration of GH shows no effect on JAK2 phosphorylation, but when combined with low 0.3 μm GHRp (that as well has no effect on its own), JAK2 activation is increased approximately four times.

FIG. 18 demonstrates that GHRp enhances the phosphorylation of STAT5. STAT5 is molecule downstream of JAK2 in a signaling pathway of the GH. The putative mechanism is that the receptors dimerize (or multimerize), JAK2 associates with the multimerized receptors and becomes phosphorylated. JAK2 can then associate with STAT5, which also becomes activated by phosphorylation. Cells were stimulated with different concentrations of GHRp or GH as indicated at the top of the panel, IP with anti-STAT5 and then WB with anti-PY (upper panel) and anti-STAT5 (lower panel). Increasing phosphorylation of STAT5 is observed as the dose of added GHRp was increasing. The same band of phosphorylation was observed when cells were stimulated with GH indicating specific signaling through GHR. Lower panel demonstrates that all the immunoprecipitates contained the same amount of STAT5 protein.

Figure 19:
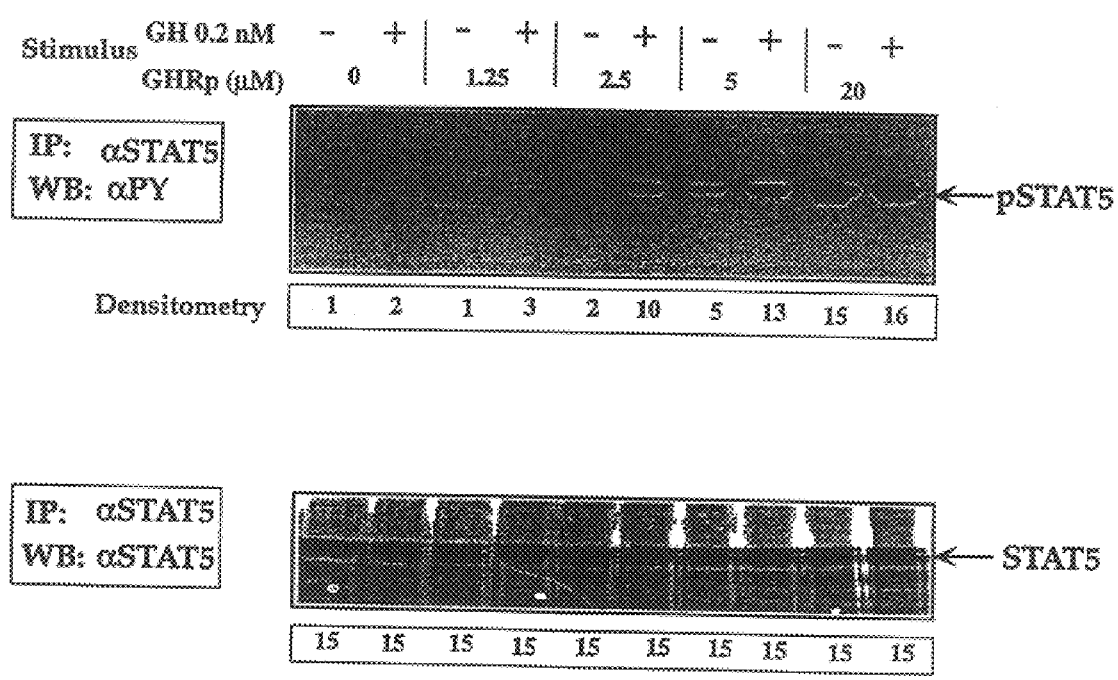

FIG. 19 demonstrates that GHRp together with GH has a synergistic effect on activation (phosphorylation) of STAT5. Stimulation of the cells with 0.2 nM GH in the presence or absence of GHRp shows significant increase in STAT5 phosphorylation, e.g., no phosphorylation is observed with 0.2 nM GH or 1.25 $\mu$M GHRp alone, but the signal is increased when both compounds are present. In addition, a weak signal of STAT5 protein phosphorylation with 2.5 $\mu$M peptide is strongly increased by presence of 0.2 nM GH. Activity was measured with anti-PY antibody (upper panel). The lower panel demonstrates that the same amount of STAT5 is present in all the immunoprecipitates. Thus, GHRp has very strong synergistic effect on GH, measured by STAT5 phosphorylation.

Figure 20:
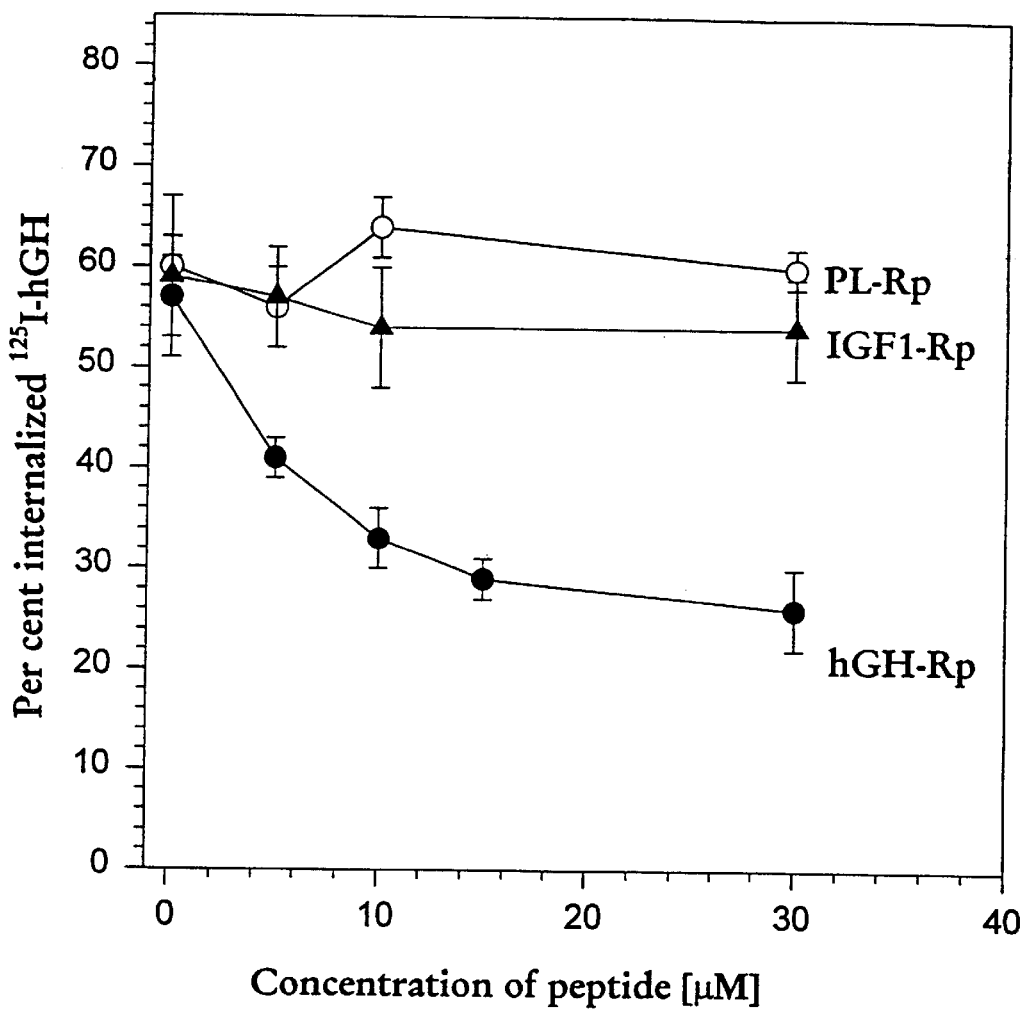

FIG. 20 shows the selectivity of GHRp for the GH-Receptor. Internalization of [$^{125}$]-GH was measured in IM9 cells in the presence of GHRp, IGF-IRP (peptide selective and active on IGF-IR; SEQ ID NO:5) and Pl-Rp (peptide specific for Prolactin receptor, SEQ ID NO:35; the prolactin receptor has a high level of identity (approximately 50%) to the GHR). Cells were preincubated for 30 min at 37° C., followed by addition of [$^{12}$I]-GH and different peptide concentrations as indicated. After the incubation of 20 min at 37° C., internalized ligand was measured by the method of acid wash. Cells were spun through oil mixture to separate bound from unbound ligand. Internalized ligand is calculated as percent of [$^{125}$ I]-GH resistant to acid wash (intracellular) versus the total amount of hormone bound to the cells. Thus, GHRp, selectively inhibits internalization of GH-receptor and therefore extends receptor's cell surface time.

DATABASE REFERENCES FOR NUCLEOTIDE AND AMINO ACID SEQUENCES

The complete mRNA sequence encoding the human insulin responsive glucose transporter (GLUT4) has the Genbank accession number M20747, published by Fukumoto et al. (1989) *J. Biol. Chem.* 264:7776–7779. The complete mRNA sequence encoding the human insulin receptor has the Genbank accession number A18657, published in International Patent Application No. WO/91/17253. The complete mRNA sequence encoding the human leptin receptor has the Genbank accession number U43168, and was published by Tartaglia et al. (1995) *Cell* 83:1263–1271. The DNA sequence encoding the human granulocyte colony stimulating factor (G-CSF) receptor has the EMBL accession numbers M59820, M380027, X55720 and X55721, and was published by Larsen et al. (1990) *J. Exp. Med.* 172:1559–1570. The complete sequence of the human interleukin 2(IL-2) receptor has the Swissprot accession number P01589, and was published by Leonard et al. (1984) *Nature* 311:626–631. The complete sequence of the human epidermal growth factor (EGF) receptor has the Swissprot accession number P00533, and was published by Ullrich et al. (1984) *Nature* 309:418–425. Additional Swissprot accession numbers are as follows, with the remainder of the numbers easily obtained: interleukin-6 receptor, P08887; interleukin-8 receptor-B, P25025; interleukin-8 receptor-A, P24024; interleukin-11 receptor, U32324; interleukin-12, P42701; interleukin-17 receptor, U31993; EPO receptor, P19235; and TPO receptor, P40238. The sequences for other cell surface receptors are known, and easily ascertainable by those in the art.

The sequences of known HLA and H-2 alleles may be found in Kabat et al. (1991) *Sequences of Proteins of Immunological Interest*, N.I.H. publication no. 91–3242, vol. 1, pp. 738–740, 761, 770–771, 779–780, 788–789 and 802–804.

DESCRIPTION OF THE SPECIFIC EMBODIMENTS

Generally, cell surface receptors of interest are internalized or are recycled into the cytoplasm in response to ligand binding. The present invention is based on the initial discovery that sequences on the extracellular portion of cell surface receptors, termed "internalization sequences" or "activation sequences" herein, are involved in modulation of receptor responses. Fortuitously, the activation sequences are not directly involved in ligand binding; that is, the ligand binding site is separate from the activation sequence of the receptor.

Without being bound by theory, it appears that these activation sequences are important in two distinct ways; in the modulation of receptor internalization, and/or in the modulation of activation of the receptor.

First, for some receptors, it appears that these activation sequences are involved in internalization of the receptor. That is, the addition of oligopeptides corresponding to the activation sequence of a receptor can modulate the internalization of the receptor; for example, to retard or inhibit the internalization of the receptor (although in some cases, as outlined below, antagonists could be created). This inhibition of internalization of the receptors effectively can provide for a greater number of receptors on the cell surface. This increase or stabilization of the number of receptors at the cell surface can result in increased signalling per unit of ligand. This has therapeutic relevance in a number of disease conditions where decreased ligand binding or signalling is a problem, or where the hormone is expensive or difficult to produce. For example, there are a number of diseases where hormone sensitivity is reduced or the production of the hormone is decreased, such that increased efficiency of ligand signalling is desirable. Non-insulin dependent diabetes mellitus (NIDDM) is an example of such a condition.

In addition, it has surprisingly been found that for a particular class of cell-surface receptors, termed "type 2 cell surface receptors" herein, the activation sequence can be important in the activation of the receptor, i.e. the activation of the signalling pathway of the receptor. Thus, oligopeptides corresponding to a receptor's activation sequence can actually replace the requirement for the ligand, and will cause receptor activation even in the absence of ligand. That is, even though the binding site for the hormone ligand and the activation sequence are different, the addition of the activation sequence oligopeptide will cause receptor activation. Without being bound by theory, it appears that type 2 cell surface receptors occur as monomeric units, each with a distinct ligand binding site and an internalization or activation site. Generally, two monomeric receptors are brought together by the binding of a single ligand molecule; this non-covalent "dimerization" is what activates the receptor and allows the downstream biological function which is the result of ligand binding. Surprisingly, the present invention reveals that this dimerization and subsequent receptor activation can occur upon the binding of the activation sequence oligopeptide, in the absence of ligand. In addition, the effect of the ligand and the effect of the activation oligopeptide is signficantly synergistic, and can allow maximum signal using reduced concentrations of each. These oligopeptides can thus be utilized either as a ligand replacement, or to increase the response of a given amount of ligand. In addition, as more fully described below, the present invention also allows the creation of antagonists to receptor signalling.

Preferably, an internalization or activation peptide will be derived from the sequence of the receptor that is to be modulated. The sequence of interest corresponds to the region of the receptor on the extracellular surface, but usually is not directly involved in ligand binding, i.e. contact is not made with the ligand (that is, there is no effect on the $K_D$ of the ligand). It should be noted that the activation sequences from different receptors are highly specific; in general, an activation sequence from one receptor will not activate a different receptor. Sequences of receptors, and positioning of the receptors in the cell membrane are known in the art. Such information may be accessed through public databases, as previously cited.

In a preferred embodiment, the sequences and receptors described herein are from humans; although as will be appreciated by those in the art, the present invention may be useful in the creation and elucidation of animal models of human disease. Accordingly, sequences and receptors from rodents (rats, mice, hamsters, guinea pigs, etc.), primates, farm animals (cows, sheep, pigs, goats, etc.) may also be used. In addition, sequences from one organism may be tested in other organisms; for example, rat sequences may be tested in humans, etc.

Accordingly, the present invention provides regulatory oligopeptides comprising activation sequences that have an amino acid sequence at least substantially identical to the sequence of a portion of a cell surface receptor extracellular domain. Generally, these oligopeptides also have sequence similarity to bioactive oligopeptides of the major histocompatibility locus class I antigens (described in U.S. Pat. No. 5,385,888, herein incorporated by reference). The oligopeptides modulate the effect of ligand binding to the corresponding receptor, thereby enhancing the physiological effect of the ligand, and may, as outlined above, act to replace the ligand requirement entirely, depending on the characterization of the receptor.

The activation sequences are initially identified by homology to the sequence of an $\alpha_1$-domain of an MHC Class I antigen. MHC Class I antigens include human MHC Class I antigens and mammalian equivalents thereof, such as Class I antigens of the H-2 locus of mice, in particular H-2 D and K. Human MHC Class I antigens include HLA-A, B and C. Of more particular interest are the amino acid sequences in the polymorphic regions of the α-1 domain, more particularly amino acids 55 to 90, usually 60 to 90, more particularly 62 to 90. The region 60–85 of the α-1 domain, more particularly 62–85 or 72–82 are found to be of particular interest. One MHC sequence of particular interest is ERETQIAKGNEQSFRVDLRTLLR, (SEQ ID NO:1; U.S. Pat. No. 5,385,888). Thus, oligopeptides with sequence similarity to these regions are preferred.

Using these sequences, and in particular SEQ ID NO:1, the sequences of any number of cell surface receptors are scanned for homologous regions. Suitable cell surface receptors include, but are not limited to, insulin receptor, insulin-like growth factor receptor, growth hormone receptor, glucose transporters (particularly GLUT 4 receptor), transferrin receptor, epidermal growth factor receptor, low density lipoprotein receptor, high density lipoprotein receptor, epidermal growth factor receptor, leptin receptor, interleukin receptors including IL-1, IL-2, IL-3, IL-4, IL-5, IL-6, IL-7, IL-8, IL-9, IL-11, IL-12, IL-13, IL-15, and IL-17 receptors, human growth hormone receptor, VEGF receptor, PDGF receptor, EPO receptor, TPO receptor, ciliary neurotrophic factor receptor, prolactin receptor, and T-cell receptors. In addition, there are a number of "orphan" receptors for which biological function has not yet been fully assigned; these are referenced herein by their SwissProt reference numbers and include, but are not limited to, SwissProt ML1B (rat melatonin receptor type 1B); SwissProt SCRC (human secretin receptor precursor); SwissProt NY1R (Xenopus nueropeptide Y receptor); SwissProt PAFR (rat platelet activating factor receptor); and SwissProt BLR1 (Burkitt's Lymphoma receptor for human, mouse and rat). Algorithms for sequence analysis are known in the art, and include, but are not limited to, the Best Fit sequence program described by Devereux et al, *Nucl. Acid Res.* 12:387–395 (1984), with default settings preferred; BLAST, described in Altschul et al. (1990) *J. Mol. Biol.* 215:403–10; ADVANCE and ADAM, described in Torelli and Robotti (1994) *Comput. Appl. Biosci.* 10:3–5; and FASTA, described in Pearson and Lipman (1988) *P.N.A.S.* 85:2444–8. The sequence similarity may be determined using the Wisconsin Package, version 8.0-OpenVMS, Genetics Computer Group.

Preferably, the amino acid sequence of the receptor region of interest will have at least about 10% sequence identity, and frequently at least about 15–20% sequence identity. The sequence similarity will be at least about 30%, with at least about 35% being preferred, and frequently at least about 45–50%. The examples provide the results of exemplary similarity searches.

Exemplary activation amino acid sequences of interest include, but are not limited to:

1. TWLGRQGPEGPSSIPPGTLTTLW (SEQ ID NO:2) from human glucose transporter, GLUT4, which is 13% identical and 39% similar to SEQ ID NO:1;
2. KTDSQILKELEESSFRKTFEDYLH (SEQ ID NO:3) from human insulin receptor, which is 35% identical and 56% similar to SEQ ID NO:1;
3. EAEAAVATQETSTVRLKVSSTAVRT (SEQ ID NO:4) from human LDL receptor, which is 16% identical and 88% similar to SEQ ID NO:1;
4. KTEAEKQAEKEEAEYRKVFENFLH (SEQ ID NO:5) from human insulin like growth factor receptor, which is 32% identical and 54% similar to SEQ ID NO:1;
5. KKENKIVPSKEIVWWMNLAEKIP (SEQ ID NO:6) from human leptin receptor, which is 17% identical and 43% similar to SEQ ID NO:1;
6. EKKPVPWESHNSSETCGLPTLVQTY (SEQ ID NO:7) from human GCSF receptor;
7. GPHCVKTCPAGVMGENNTLVWKY (SEQ ID NO:8) from human epidermal growth factor receptor, which is 17% identical and 43% similar to SEQ ID NO:1;
8. EYELQYKEVNETKWKMMDPILTTSVPVY (SEQ ID NO:9) from human growth factor receptor, which is 32% identical and 48% similar to SEQ ID NO:1;

9. ARGGTLELRPRSRYRLQLRARLN (SEQ ID NO:10) from human thrombopoietin receptor, which is 22% identical and 43% similar to SEQ ID NO:1;
10. QRVEILEGRTECVLSNLRGRTRY (SEQ ID NO:11) from human erythropoietin receptor, which is 26% identical and 43% similar to SEQ ID NO:1;
11. EMQSPMQPVDQASLPGHCREPPPW, (SEQ ID NO:12) from interleukin-2 (IL-2) receptor alpha chain, which is 12% identical and 37% similar to SEQ ID NO:1;
12. DPDEGVAGAPTGSSPQPLQPL, (SEQ ID NO:13) from IL-2 receptor beta chain, which is 19% identical and 38% similar to SEQ ID NO:1;
13. QEEGANTRAWRTSLLIALGTLL (SEQ ID NO:14) from interleukin-3 (IL-3), which is 27% identical and 50% similar to SEQ ID NO:1;
14. EPSLRIAASTLKSQISYRARVRAWAQCY (SEQ ID NO:15) from interleukin-4 (IL-4) receptor, which is 28% identical and 52% similar to SEQ ID NO:1;
15. DYETRITESKCVTILHKGFSASVRTILQ (SEQ ID NO:16) from interleukin-5 (IL-5), which is 30% identical and 52% similar to SEQ ID NO:1;
16. PAQEVARGVLTSLPGDSVTL (SEQ ID NO:17) interleukin-6 (IL-6) receptor, which is 30% identical and 50% similar to SEQ ID NO:1;
17. GKSNICVKVGEKSLTCKKIDLTTIVK (SEQ ID NO:18) from interleukin-7 (IL-7), which is 26% identical and 61% similar to SEQ ID NO:1;
18. EDMGNNTANWRMLLRILPQSF (SEQ ID NO:19) from interleukin-8 (IL-8) receptor-B, which is 24% identical and 43% similar to SEQ ID NO:1;
19. EVLGNDTAKWRMVLRILPHTF (SEQ ID NO:20) from interleukin-8 (IL-8) receptor-A, which is 19% identical and 52% similar to SEQ ID NO:1;
20. ELDPGFIHEARLRVQMATL (SEQ ID NO:21) from interleukin-9 (IL-9) receptor, which is 32% identical and 63% similar to SEQ ID NO:1;
21. EVITDAVAGLPHAVRVSARDFL (SEQ ID NO:22) from interleukin-11, which is 32% identical and 45% similar to SEQ ID NO:1;
22. EQPTQLELPEGCQGLAPGTEVTYRLQLHML (SEQ ID NO:23) from interleukin-12, which is 43% identical and 67% similar to SEQ ID NO:1;
23. EWSDKQCWEGEDLSKKTLLRFW (SEQ ID NO:24) from interleukin-13, which is 27% identical and 59% similar to SEQ ID NO:1;
24. KQDKKIAPETRRSIEVPLNERI (SEQ ID NO:25) from interleukin-13 (a second sequence), which is 23% identical and 41% similar to SEQ ID NO:1;
25. DPNITVETLEAHQLRVSFTLWNESTHYQILLTSF (SEQ ID NO:26) from interleukin-17;
26. EITTDVEKIQEIRYRSKLKLI (SEQ ID NO:27) from human platelet derived growth factor (PDGF) receptor;
27. EARCDFCSNNEESFILDADSNM (SEQ ID NO:28) from human vascular endothelial growth factor (VEGF) receptor, which is 27% identical and 50% similar to SEQ ID NO:1;
28. TWQTPSTWPDPESFPLKFFLRY (SEQ ID NO:29) from human ciliary neurotrophic factor receptor-alpha, which is 27% identical and 59% similar to SEQ ID NO:1;
29. DSQTNVSQSKDSDVYITDKTVL (SEQ ID NO:30) from T-cell receptor alpha chain, which is 14% identical and 50% similar to SEQ ID NO:1;
30. EWTQDRAKPVTQIVSAEAWGRADC (SEQ ID NO:31) from T-cell receptor beta chain, which is 17% identical and 37% similar to SEQ ID NO:1;
31. SQEGNTMKTNDTYMKFSWLTVPEESLD-KEHRCIVRH (SEQ ID NO:32) from T-cell receptor gamma chain, which is 29% identical and 50% similar to SEQ ID NO:1;
32. VHTEKVNMMSLTVLGLRMLF (SEQ ID NO:33) from T-cell receptor delta chain, which is 37% identical and 58% similar to SEQ ID NO:1;
33. EKTDRFVMKKLNDRVMRVEYHFLSPY (SEQ ID NO:34) from human transferrin receptor, which is 29% identical and 54% similar to SEQ ID NO:1;
34. EWEIHFAGQQTEFKILSLHPGQKYL (SEQ ID NO:35) from human prolactin receptor, which is 20% identical and 48% similar to SEQ ID NO:1.

In addition, as outlined below, there are a number of "orphan" receptors, for which specific function has not yet been associated, that may be included in the invention. The activation sequences of these are as follows:

35. ARRKAKAERKLRLRPSDLRSFLTMF (SEQ ID NO:38) from rat melatonin receptor type 1B.
36. KLRTQETRGNEVSHYKRLARSTLLLIP (SEQ ID NO:39) from human secretin receptor.
37. GKYVCLEDFPEDKRFLSYTTLLFIL (SEQ ID NO:40) from Xenopus neuropeptide Y receptor type 1.
38. SFRVDSEFRYT (SEQ ID NO:41) from rat platelet activating factor receptor.
39. CLNPMLYTFAGVKFRSDLSRLLTKL (SEQ ID NO:42) from human Burkitt's lymphoma receptor.
40. CLNPMLYTFAGVKRFSDLSRLLTKL (SEQ ID NO:43) from mouse Burkitt's lymphoma receptor.
41. CLNPMLYTFAGVKRFSDLSRLLTKL (SEQ ID NO:44) from rat Burkitt's lymphoma receptor.

The receptor sequence of interest, i.e. the activation sequence, will comprise, as an active motif sequence, at least 8 amino acids, usually at least about 12 amino acids, more usually at least about 18 amino acids, and fewer than about 40 amino acids, more usually fewer than 30 amino acids.

In a preferred embodiment, oligopeptides are made, either synthetically or through recombinant means, which correspond to the activation sequence of the extracellular domain of the cell surface receptor. By "corresponds" herein is meant either that the oligopeptide is identical to all or part of the activation sequence, or that the oligopeptide has substantial homology to the activation sequence; that is, as described below, the oligopeptide may have amino acid substitutions, insertions or deletions as compared to the activation sequence.

As will be appreciated by those in the art, the activation sequences may be modified, either as modified oligopeptides or as modified receptors, where the receptors are made with modified activation sequences.

In a preferred embodiment, the activation sequences of the regulatory oligopeptides are altered. Preferably, any modifications do not substantially alter the biological activity, i.e. they do not inhibit internalization or aggregation, or prevent activation, of the activation sequence for the corresponding receptor. This is easily tested using the binding assays described herein. For example, amino acid substitutions, insertions and deletions may be made.

In one embodiment, amino acid substitutions are made. In general, it is preferable that residues critical for biological activity are either not altered or conservatively altered. Critical residues may be elucidated using known mutagenesis techniques followed by activity or binding assays; for example, using scanning mutagenesis techniques, wherein single amino acid residues within the activation sequence are modified by substitution with an aliphatic amino acid, e.g. scrine, alanine, glycine, valine, etc.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the oligopeptide are desired, substitutions are generally made in accordance with the following chart:

Chart I

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I, although these generally are not preferred. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

In a preferred embodiment, not more than about three substitutions or deletions will be made, and that the change will not be more than about 20 number %, usually not more than about 10 number %, of the number of amino acids in the active motif, although in some instances higher numbers of alterations may be made. In some cases, it may be desirable to make antagonist peptides, that will bind but not activate the receptor, in which case more alterations may be made. In a preferred embodiment, the present invention provides oligopeptides that have at least about 60% identical homology to the activation sequence of each receptor described herein, with at least about 75% being preferred and at least about 80% being especially preferred; in some instances the identity will be as high as 90 to 95 or 98%.

However, if only non-critical residues are altered, this may be higher. Similarly, if the biological function of the activation sequence is to be decreased, the amount of changes may also be greater. Preferred are conservative substitutions, as known in the art, including substitutions within the large hydrophobic group: isoleucine, leucine, valine and phenylalanine; between serine and threonine; glycine and alanine; asparagine and glutamine; aspartic acid and glutamic acid; or lysine, arginine and histidine. In some embodiments, non-conservative alterations are done.

In addition to modifications within the activation sequences, the oligopeptides may contain additional sequences, as will be appreciated by those in the art. For example, the oligopeptides may be extended to: 1) provide convenient linking sites, e.g. cysteine or lysine; 2) to enhance stability; 3) to bind to particular receptors; 4) to provide for site-directed action; 5) to provide for ease of purification (for example, epitope or purification ($His_6$) tags); 6) to alter the physical characteristics (e.g. solubility, charge, etc.); or 7) to stabilize the conformation; etc. The oligopeptides may be joined to non-wild-type flanking regions as fused proteins, joined either by linking groups or covalently linked through cysteine (disulfide) or peptide linkages. The oligopeptide may be linked through a variety of bifunctional agents, such as maleimidobenzoic acid, methyidithioacetic acid, mercaptobenzoic acid, S-pyridyl dithiopropionate, etc. The oligopeptides may be joined to a single amino acid at the N- or C-terminus of a chain of amino acids, or may be internally joined. For example, the subject peptides may be covalently linked to an immunogenic protein, such as keyhole limpet hemocyanin, ovalbumin, etc. to facilitate antibody production to the subject oligopeptides.

In a preferred embodiment, the oligopeptides may be shorter than those depicted herein; that is, residues from either the N- or C-terminus of the oligopeptide may be deleted with the retention of biological activity, preferably full biological activity. In some cases, internal residues may be removed from the oligopeptide. Generally, this will be done by sequentially removing residues and assaying for the ability to bind to the activation sequence of a receptor; once binding has been established, activation may be evaluated.

Alternatively, the subject oligopeptides may be expressed in conjunction with other peptides or proteins, so as to be a portion of the chain, either internal, or at the N- or C-terminus. Various post-expression modifications may be achieved. For example, by employing the appropriate coding sequences, one may provide farnesylation or prenylation, such that the subject peptide will be bound to a lipid group at one terminus, and will be able to be inserted into a lipid membrane, such as a liposome.

The subject oligopeptides may be modified by the addition of chemical moieties or groups. For example, the oligopeptides may be PEGylated, where the polyethyleneoxy group provides for enhanced lifetime in the blood stream. The subject oligopeptides may also be combined with other proteins, such as the Fc of an IgG isotype to enhance complement binding, or with a toxin, such as ricin, abrin, diphtheria toxin, or the like, particularly the A chain. The oligopeptides may be linked to antibodies for site directed action. For conjugation techniques, see, for example, U.S. Pat. Nos. 3,817,837; 3,853,914; 3,850,752; 3,905,654; 4,156,081; 4,069,105; and 4,043,989, which are incorporated herein by reference. As outlined herein, the oligopeptides may be labelled as well.

Oligomers of the regulatory oligopeptides of the invention may also be made. For example, oligopeptides of interest for drug screening include, but are not limited to: 1) an oligopeptide having at least substantially the sequence of the receptor region of interest; 2) MHC/receptor oligopeptide heterodimers having the sequence of the receptor region of interest and the amino acid sequence of bioactive oligopeptides of the major histocompatibility locus class I antigens; and 3) receptor derived oligopeptide homodimers, generally as a head to tail dimer, where a spacer of from 1 to 3 small neutral amino acids may be present between the two active peptide sequences, as is generally described in WO US96/15426, specifically incorporated herein by reference.

Once identified, the oligopeptides comprising the activation sequences may be prepared in accordance with conventional techniques, such as synthesis (for example, use of a Beckman Model 990 peptide synthesizer or other commercial synthesizer). Peptides may be produced directly by recombinant methods (see Sambrook et al. *Molecular Cloning: A Laboratory Manual*, CSHL Press, Cold Spring Harbor, N.Y., 1989) or as a fusion protein, for example to a protein that is one of a specific binding pair, allowing purification of the fusion protein by means of affinity reagents, followed by proteolytic cleavage, usually at a site engineered to yield the desired peptide (see for example Driscoll et al. (1993) *J. Mol. Bio.* 232:342–350).

In a preferred embodiment, the activation sequence contained within the receptor is altered, to form a modified receptor. In a modified form of the receptor, the sequence corresponding to the regulatory peptide (i.e. the activation sequence) contains an insertion, substitution or deletion, such that the ability of the receptor to internalize in response to ligand binding is altered. The modification may include a deletion or substitution of the complete oligopeptide sequence, or a portion thereof. Substitutions of interest also include scanning mutations as outlined above.

Conveniently, the modification is performed using recombinant DNA technology. The DNA sequence encoding the desired receptor may be obtained from various sources, or may be obtained from a cDNA library using probes derived from publically available sequence information. Techniques for in vitro mutagenesis of cloned genes are known; methods for site specific mutagenesis can be found in Sambrook, et al. supra. pp 15.3–15.108; Weiner et al. (1993) *Gene* 126:3541; Sayers et al. (1992) *Biotechniques* 13:592–6; Jones and Winistorfer (1992) *Biotechniques* 12:528–30; Barton et al. (1990) *Nucleic Acids Res.* 18:7349–55; Marotti and Tomich (1989) *Gene Anal. Tech.* 6:67–70 and Zhu (1989) *Anal. Biochem.* 177:1204. For example, to delete a sequence, primers are devised that span the region. On hybridization, the region to be deleted forms a single stranded loop. The loop may be excised by nuclease digestion, or a suitable polymerase may be used to extend out from the primer.

For expression, the DNA sequences are inserted into an appropriate expression vector, where the native transcriptional initiation region may be employed or an exogenous transcriptional initiation region, i.e., a promoter other than the promoter which is associated with the gene in the normally occurring chromosome. The promoter may be introduced by recombinant methods in vitro, or as the result of homologous integration of the sequence into a chromosome. A wide variety of transcriptional initiation regions are known for a wide variety of expression hosts. Generally a selectable marker operative in the expression host will be present. The promoter may be operably linked to the coding sequence of the genes of interest so as to produce a translatable mRNA transcript. Expression vectors have convenient restriction sites located near the promoter sequence so as to provide for the insertion of nucleic acid sequences encoding heterologous proteins. The promoters in suitable expression vectors may be either constitutive or inducible. Expression vectors for the production of fusion proteins, where the exogenous fusion peptide provides additional functionality, i.e. increased protein synthesis, stability, reactivity with defined antisera, an enzyme marker, e.g., b-galactosidase, etc.

The expression vectors are transformed into a host cell. The expression hosts may involve prokaryotes or eukaryotes, particularly *E. coli; B. sublilis;* yeast cells; mammalian cells; e.g., COS and CHO cells, HeLa cells, L(tk–), primary cultures; insect cells; *Xenopus laevis* oocytes; and the like. Particularly preferred host cells are mammalian cells.

Once made, the oligopeptides and modified receptors find use in a number of applications.

In a preferred embodiment, the oligopeptides are used in methods for inhibiting the internalization of a cell surface receptor response of a mammalian cell. The methods comprises adding oligopeptides as defined herein to mammalian cells expressing the cell surface receptor. Upon addition (either simultaneous or sequential) of the ligand which binds the receptor, the oligopeptide inhibits the receptor internalization. Alternatively, for ligand-independent type-2 receptors, as outlined below, the ligand need not be added to alter receptor internalization.

In a preferred embodiment, the oligopeptides are used in methods of activating receptors. As discussed above, for some receptors, the addition of the oligopeptide can replace or augment the requirement for ligand binding to effect receptor activation. As outlined briefly above, cell-surface receptors appear to fall into two general classes: type 1 and type 2 receptors. Type 1 receptors have generally two identical subunits associated together, either covalently or otherwise, in the absence of bound ligand; they are essentially preformed dimers, even in the absence of ligand. The type 1 receptors include the insulin receptor and the IGF receptor. The type-2 receptors, however, generally are in a monomeric form, and rely on either binding of one ligand to each of two monomers, or, as shown in the present invention, the binding of one or more oligopeptides that result in multimer formation, to achieve receptor activation. Type-2 receptors include the growth hormone receptor, the leptin receptor, the LDL receptor, the GCSF receptor, the interleukin receptors including IL-1, IL-2, IL-3, IL-4, IL-5, IL-6, IL-7, IL-8, IL-9, IL-I 1, IL-12, IL-13, IL-15, IL-17, etc., receptors receptor, EPO receptor, TPO receptor, VEGF receptor, PDGF receptor, T-cell receptor, transferrin receptor, prolactin receptor, and the ciliary neurotrophic factor receptor. Thus, the present invention provides receptors with exogeneous compounds bound to their activation sequences, and specifically with bound oligopeptides as defined herein.

As is known in the art, the monomeric nature of these type 2 receptors can result in unusual saturation kinetics. For example, it is known for growth hormone that saturation, leading to reduction in activation, can occur at high levels of administered growth hormone. This is presumably due to the fact that since there is only one ligand binding site per monomeric receptor, at high levels of ligand, each individual receptor monomer can bind a ligand molecule, and thus will not be brought together into a dimer form; that is, each monomer has a bound ligand, rather than two monomers sharing a ligand.

A receptor may be classified as either type 1 (ligand dependent) or type 2 (ligand independent) on the basis of several tests. As noted above, type 2 receptors will exhibit a decrease in receptor activation at high levels of ligand. Type 2 receptors may also be classified as such using the present invention, since the addition of the internalization oligopeptides of the invention will result in receptor activation even in the absence of ligand.

As discussed herein, oligopeptides based on the activation sequences of type 2 cell-surface receptors result in activation of the receptor even in the absence of ligand. It is important to note in this case that the ligand binding site is distinct from the activation or activation sequence. Thus, the present invention provides methods for activating a type 2 cell surface receptor by binding an exogeneous compound to the activation sequence of the receptor. As a result of this binding, two monomeric receptors dimerize and activate the receptor. However, in an alternate embodiment, activation may be prevented by binding an antagonistic exogeneous agent to the activation sequence to prevent activation of the receptor; that is, certain agents will prevent activation of the receptor, even in the presence of ligand.

By "exogeneous compound" herein is meant a compound not produced endogeneously by the cell or organism; that is, it is artificially introduced to the cell or organism. Exogeneous compounds include, but are not limited to, bioactive agents as defined below such as chemical and small organic moieties; and the oligopeptides described herein. As will be appreciated by those in the art and described below, having determined the location of the binding, and the mechanism of receptor activation by binding, it will be routine to screen for other molecules that will accomplish the same thing as the oligopeptides of the invention. This may be done by finding exogeneous agents that will simultaneously bind at least two monomeric receptors, causing activation, or by finding an agent that will bind the internalization (activation) sequence of the receptor and then making multimers (i.e. dimers) of this binding agent. A preferred embodiment utilizes the oligopeptides of the invention as the exogeneous compounds.

By "receptor activation" or grammatical equivalents herein is meant the biological function associated with ligand binding to a cell-surface receptor. As will be appreciated by those in the art, this will vary widely depending on the identity of the receptor. For example, cell-surface receptors frequently cause phosphorylation as a result of ligand binding, that generally, although not always, is due to a conformational change in the receptor as a result of ligand binding. Thus "activation" may comprise a conformational change either within the receptor, or as a result of monomeric receptors becoming multimeric, which allows the receptor do facilitate signalling. For example, this conformational change may allow the receptor to become phosphorylated, or allow the receptor to associate with a third molecule which then results in phosphorylation of either the receptor, the third molecule, or yet another molecule. In this way signalling is accomplished.

In a preferred embodiment, the exogeneous compound is added to the cell in the absence of exogeneous ligand. By "exogeneous ligand" herein is meant ligand which is not produced endogeneously by the cell or organism; i.e. exogeneous ligand is introduced to the cell or organism. It will be appreciated that the composition of the ligand is generally the same, whether produced endogeneously or introduced exogeneously; the designation goes to the source of the ligand, not its composition. As will be appreciated by those in the art, there may or may not be endogeneous ligand present. The exogeneous compound acts as a ligand replacement, although it does not bind to the ligand binding site as a competitor; rather, as outlined herein, it binds to the activation sequence of the receptor. The presence or absence of binding of the exogeneous compound may be tested in a variety of ways, as will be appreciated by those in the art, including labeling the exogeneous compound and detecting labelled receptors, competitive assays with known binding agents, such as the oligopeptides of the invention, or by utilizing modified receptors which do not contain activation sequences.

In a preferred embodiment, the exogeneous compound is added to the receptor in the presence of the ligand which normally activates the receptor. Again, as above, there may be endogeneous ligand present, or exogeneous ligand added in addition to the exogeneous compound. In this embodiment, the level of receptor activation is greater with a combination of the ligand and the exogeneous compound as compared with the same amount of ligand alone. In fact, surprisingly, for some receptors there appears to be a synergistic effect; that is, the effect of adding ligand and exogeneous compound (in this case, an oligopeptide of the invention), is greater than either ligand alone or exogeneous compound alone, as is generally shown in the examples and Figures. Without being bound by theory, it appears that this may be due to the fact that the oligopeptides bind to receptors that do not have bound ligand, and to those that do, and putatively retard internalization as well. Accordingly, it may be desirable to add some exogeneous ligand with the exogeneous compounds of the invention.

Accordingly, in a preferred embodiment, the oligopeptides are administered therapeutically. The subject oligopeptides act to enhance the cellular response to hormones that bind to the surface membrane receptor corresponding to the oligopeptide, e.g. insulin response is enhanced by the oligopeptide SEQ ID NO:3, glucose transport is enhanced by the oligopeptide SEQ ID NO:2, etc. Hormones including insulin, insulin-like growth factor, human growth hormone, glucose transporters, transferrin, epidermal growth factor, EPO, TPO, low density lipoprotein, human growth hormone and interleukins are herein referred to as "therapeutic hormones" or "ligands". Enhancement of the cellular response to therapeutic hormones by the subject oligopeptides provides a means of improving the response of patients that are either unresponsive, e.g. resistant, to the action of such hormones, or, in the case of the type 2 receptors, the oligopeptides can actually serve as ligand replacements. This is particularly desirable in some situations where the administration of the hormone ligand has undesirable side-effects, for example in the case of growth hormone; the use of the oligopeptides or other exogeneous compounds may allow receptor activation without significant side-effects.

In one embodiment, the subject oligopeptides may be administered to patients requiring enhancement of the response to naturally occurring levels of the therapeutic hormone.

Alternatively, the oligopeptides may be administered to patients in conjunction with a therapeutic hormone. Of particular interest is the treatment of insulin resistance, which may be associated with defects in glucose transport, or in the cellular response to insulin. Administration of the subject oligopeptides improves the response to insulin therapy. Similarly, enhancement of the effect of human growth hormone is also of particular interest. Human growth hormone is current given in a number of clinical situations as an injectible drug; alternative therapies may include augmenting the response of endogeneous hormone.

Similarly, for type 2 cell surface receptors, exogeneous compounds, including the oligopeptides of the invention, may be administered to patients either as ligand replacements, or to augment the response of a given amount of ligand hormone, as is outlined above. Thus, the present invention provides for methods of treating patients with disorders associated with a ligand that normally activates a type 2 cell surface receptor. For example, patients with either insufficient amounts of growth hormone, no growth hormone, or insufficient response to a normal level of growth hormone, may all be treated by the administration of an exogeneous compound which binds to the activation sequence of the growth hormone receptor and causes both receptor activation and retarded receptor internalization. Similarly, other disorders such as obesity or weight problems associated with leptin may be treated. It should be noted that diseases associated with both not enough ligand present in the patient, and too much ligand present in the patient, may be treated using the exogeneous compounds of the invention. For example, when there is too much ligand present in the patient, for example into the ranges where ligand saturation is seen, the addition of the exogeneous compounds, for example the oligopeptides of the invention, can allow dimerization of the receptor and activation can actually cause the body to make less ligand.

When the exogeneous compound or the oligopeptide is to be administered with exogeneous ligand, the administration can be simultaneous or sequential, as will be appreciated by those in the art.

For therapy, when the oligopeptides are to be used, the oligopeptides may be administered topically or parenterally, e.g. by injection at a particular site, for example, subcutaneously, intraperitoneally, intravascularly, intranasally, transdermally or the like. Formulations for injection will comprise a physiologically-acceptable medium, such as water, saline, PBS, aqueous ethanol, aqueous ethylene glycols, or the like. Water soluble preservatives which may be employed include sodium bisulfite, sodium thiosulfate, ascorbate, benzalkonium chloride, chlorobutanol, thimerosal, phenylmercuric borate, parabens, benzyl alcohol and phenylethanol. These agents may be present in individual amounts of from about 0.001 to about 5% by weight and preferably about 0.01 to about 2%. Suitable water soluble buffering agents that may be employed are alkali or alkaline earth carbonates, phosphates, bicarbonates, citrates, borates, acetates, succinates and the like, such as sodium phosphate, citrate, borate, acetate, bicarbonate and carbonate. Additives such as carboxymethylcellulose may be used as a carrier in amounts of from about 0.01 to about 5% by weight. The formulation will vary depending upon the purpose of the formulation, the particular mode employed for modulating the receptor activity, the intended treatment, and the like. The formulation may involve patches, capsules, liposomes, time delayed coatings, pills, or may be formulated in pumps for continuous administration. The specific dosage can be determined empirically in accordance with known ways. See, for example Harrison's, Principles of Internal Medicine, 11th ed. Braunwald et al. ed, McGraw Hill Book Co., New York, 1987.

Generally, a therapeutically effective dose of the subject oligopeptides will be in the range of about 0.005–10, more usually from about 0.01-1 mg/kg of host weight, and preferably from about 0.1 to about 1 mg/kg; for example, from about 0.3 to about 0.9 is preferred for the leptin receptor oligopeptide. Such a dose will be sufficient to enhance the action of the therapeutic hormone, usually by at least as much as 50%. Administration may be as often as daily; usually not more than one or more times daily, or as infrequent as weekly, depending upon the level of drug which is administered. The oligopeptides may be administered alone, or in combination with the therapeutic hormone. The hormone may be administered at a normally therapeutically effective dose, or the dose may be decreased by as much as 50%, usually by as much as 25%, to compensate for the oligopeptide enhancement. The host may be any mammal including domestic animals, pets, laboratory animals and primates, particularly humans. The amount will generally be adjusted depending upon the half life of the peptide, where dosages in the lower portion of the range may be employed where the peptide has an enhanced half life or is provided as a depot, such as a slow release composition comprising particles, introduced in a matrix which maintains the peptide over an extended period of time, e.g., a collagen matrix, use of a pump which continuously infuses the peptide over an extended period of time over a substantially continuous rate, or the like. Heller, *Biodegradable Polymers in Controlled Drug Delivery,* in: CRC Critical Reviews in Therapeutic Drua Carrier Systems, Vol. 1, CRC Press, Boca Raton, Fla., 1987, pp 39–90, describes encapsulation for controlled drug delivery, and Di Colo (1992) *Biomaterials* 13:850–856 describes controlled drug release from hydrophobic polymers.

In a preferred embodiment, the oligopeptides, modified receptors and cells containing the modified receptors are used in screening assays. Identification of the amino acid sequence in this region of receptors permits the design of drug screening assays for compounds that modulate receptor internalization or serve as ligand replacements for type 2 receptors.

Drug screening assays utilize the subject sequence information and peptide compositions, e.g., proteins, oligopeptides and synthetic derivatives thereof, to identify agents that modulate the internalization of cell surface receptors, or, in the case of type 2 receptors, allow the identification of agents that serve as ligand replacements.

Drug candidates capable of modulating surface receptor internalization are identified by first screening the drug candidates for the ability to compete with a bioactive oligopeptide for association with the intact receptor or that interfere with the binding of an oligopeptide to the subject receptor derived oligopeptides.

Thus, in a preferred embodiment, the methods comprise combining a cell surface receptor which contains an activation sequence and a candidate bioactive agent, and determining the binding of the candidate agent to the activation sequence. By "cell surface receptor" herein is meant any of number of cell surface receptors which are usually internalized upon ligand binding. Suitable cell surface receptors are as outlined above. Preferred embodiments utilize the human cell surface receptors, although other mammalian receptors may also be used, including rodents (mice, rats, hamsters, guinea pigs, etc.), farm animals (cows, sheep, pigs, horses, etc.) and primates. This latter embodiments may be preferred in the development of animal models of human disease. Included within the definition of cell surface receptors are amino acid substitions, insertions, or deletions of the naturally occuring sequence. Preferably, these do not alter the biological activity of the receptors, although as outlined herein, in some instances it may be desirable to modify the biological activity of the receptors.

Furthermore, included within the definition of cell surface receptors are portions of cell surface receptors; that is, either the full-length receptor may be used, or functional portions thereof. In a preferred embodiment, at least for a type 1 receptor, the functional domain comprises at least a ligand binding domain and an activation sequence, such that the conformational change that occurs upon ligand binding to the receptor will still occur. However, as outlined herein, the function domain for a type 2 receptor may comprise only the activation sequence.

Generally, in a preferred embodiment of the methods herein, the cell surface receptor is non-diffusably bound to an insoluble support having isolated sample receiving areas (e.g. a microtiter plate, an array, etc.). The insoluble supports may be made of any composition to which peptide or receptor can be bound, is readily separated from soluble material, and is otherwise compatible with the overall method of screening.

The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, teflon™, etc. Microtiter plates and arrays are especially convenient because a large number of assays can be carried out simultaneously, using small amounts of reagents and samples. The particular manner of binding of the peptide or other protein is not crucial so long as it is compatible with the reagents and overall methods of the invention, maintains the activity of the peptide and is nondiffusable. Preferred methods of binding include the use of antibodies (which do not sterically block either the ligand binding site or activation sequence when the receptor is bound to the support), direct binding to "sticky" or ionic supports, chemical crosslinking, the synthesis of the receptor on the surface, etc. Following binding of the peptide or receptor, excess unbound material is removed by washing. The sample receiving areas may then be blocked through incubation with bovine serum albumin (BSA), casein or other innocuous protein.

In a preferred embodiment, particularly for type-1 receptor assays, a ligand or analog bound by the cell surface receptor will also be added to the assay. That is, when insulin receptors are used, the ligand is insulin; when human growth hormone receptors are used, the ligand is human growth hormone; etc. As will be appreciated by those in the art, ligand analogs may also be used. In a preferred embodiment, this is not required, for example when assaying type-2 receptors.

A candidate bioactive agent is added to the assay. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The term "agent" or "exogeneous compound" as used herein describes any molecule, e.g., protein, oligopeptide, small organic molecule, polysaccharide, polynucleotide, etc., with the capability of directly or indirectly altering cell surface receptor internalization and/or activation, which can be in response to ligand binding or in the absence of ligand binding. Generally a plurality of assay mixtures are run in parallel with different agent concentrations to obtain a differential response to the various concentrations. Typically, one of these concentrations serves as a negative control, i.e., at zero concentration or below the level of detection.

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

The determination of the binding of the candidate bioactive agent to the receptor may be done in a number of ways. In a preferred embodiment, the candidate bioactive agent is labelled, and binding determined directly. For example, this may be done by attaching all or a portion of the cell-surface receptor to a solid support, adding a labelled candidate agent (for example a fluorescent label), washing off excess reagent, and determining whether the label is present on the solid support. Various blocking and washing steps may be utilized as is known in the art.

By "labeled" herein is meant that the compound is either directly or indirectly labeled with a label which provides a detectable signal, e.g. radioisotope, fluorescers, enzyme, antibodies, particles such as magnetic particles, chemiluminescers, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the oligopeptides may be labeled at tyrosine positions using $^{125}$I (for example, the activation sequences of the human GLUT4, insulin, IGF-1, G-CSF, IL-2 and hGH receptors all contain tyrosine residues), or with fluorophores. Alternatively, more than one component may be labeled with different labels; using $^{125}$I for the oligopeptides, for example, and a fluorophor for the candidate agents.

In a preferred embodiment, the binding of the candidate bioactive agent is determined through the use of competitive binding assays. In this embodiment, the competitor is an oligopeptide as described herein.

In one embodiment, the candidate bioactive agent is labeled. Either the candidate bioactive agent, or the oligopeptide, is added first to the receptor for a time sufficient to allow binding, if present. Incubations may be performed at any temperature which facilitates optimal activity, typically between 4 and 40° C. Incubation periods are selected for optimum activity, but may also be optimized to facilitate rapid high through put screening. Typically between 0.1 and 1 hour will be sufficient. Excess reagent is generally removed or washed away. The second component is then added, and the presence or absence of the labeled component is followed, to indicate binding.

In a preferred embodiment, the oligopeptide is added first, followed by the candidate bioactive agent. Displacement of the oligopeptide is an indication that the candidate bioactive agent is binding to the activation sequence and thus is capable of modulating the internalization of the receptor. In this embodiment, either component c an be labeled. Thus, for example, if the oligopeptide is labeled, the presence of label in the wash solution indicates displacement by the agent. Alternatively, if the candidate bioactive agent is labeled, the presence of the label on the support indicates displacement.

In an alternative embodiment, the candidate bioactive agent is added first, with incubation and washing, followed by the oligopeptide. The absence of binding by the oligopeptide may indicate that the bioactive agent is bound to the receptor with a higher affinity. Thus, if the candidate bioactive agent is labeled, the presence of the label on the support, coupled with a lack of oligopeptide binding, may indicate that the candidate agent is capable of binding to the activation sequence and modulating the internalization of the receptor.

In a preferred embodiment, the methods comprise combining a cell surface receptor, a ligand bound by the receptor (if required), and an oligopeptide as described herein, to form a test mixture. The candidate bioactive agent is added to the test mixture, and the binding of the candidate bioactive agent to the activation sequence of the receptor is determined. In th is embodiment, either or both of the oligopeptide or the candidate bioactive agent is labeled, with preferred embodiments utilizing labeled oligopeptides, such that displacement of the label indicates binding by the candidate bioactive agent.

In a preferred embodiment, the methods comprise differential screening to identity bioactive agents that are capable of modulating the internalization or activating receptors. In this embodiment, the methods comprise combining a cell surface receptor, a ligand (if required), and an oligopeptide in a first sample. A second sample comprises a candidate bioactive agent, a cell surface receptor, a ligand (if required), and an oligopeptide. The binding of the oligopeptide is determined for both samples, and a change, or difference in binding between the two samples indicates the presence of an agent capable of binding the activation sequence and potentially modulating the internalization of the receptor. That is, if the binding of the oligopeptide is different in the second sample relative to the first sample, the agent is capable of binding the activation sequence.

Alternatively, a preferred embodiment utilizes differential screening to identify drug candidates that bind to the native receptor, but cannot bind to modified receptors, for example those that have the activation sequences deleted. The structure of the receptor sequence of interest may be modeled, and used in rational drug design to synthesize agents that interact with that site. Drug candidates that affect receptor internalization or receptor activation are also identified by screening drugs for the ability to either enhance or reduce the effect of the subject receptor derived oligopeptides on the internalization or activation of a selected surface receptor.

Screening may be performed to find agents that interfere with the association of a bioactive MHC-derived oligopeptide with the subject oligopeptides, where the agents will be capable of modulating the internalization or activating the receptors from which the subject oligopeptides are derived. This is done using the methods described above, but replacing the oligopeptides with a sequence from a $\alpha$1-domain of an MHC Class I antigen, such as SEQ ID NO:1.

The drug candidate and varying concentrations of the subject receptor-derived oligopeptides are added to each of the sample receiving areas containing support-bound peptide. The oligopeptide added is of substantially the same amino acid sequence as the oligopeptide bound to the support and is labeled.

Positive controls for binding of active peptide and competitive binding of active peptide may include samples containing labeled active peptide alone and a mixture of labeled active peptide and unlabeled active peptide, respectively. Samples containing labeled active peptide and unlabeled inactive peptide that does not aggregate with the bound peptide may serve as a negative control for competitive binding with peptide. Preferably all control and test samples are performed in at least triplicate to obtain statistically significant results. Incubation of all samples is for a time sufficient for the binding of the labeled active peptide to the support-bound peptide. Following incubation, all samples are washed free of non-specifically bound material and the amount of bound, labeled peptide determined. For example, where a radiolabel is employed in labeling the peptide, the samples may be counted in a scintillation counter to determine the amount of bound, labeled peptide.

In test samples containing the drug candidate, if the amount of labeled active peptide bound to the support-bound peptide or receptor is in the range of values of the positive control samples for competitive binding and is significantly less than the negative control samples for competitive binding, then the drug candidate in the test sample is able to successfully competitively bind the support-bound peptide. Drug candidates capable of such competitive binding may mediate modulation of cell surface expression of a receptor.

A variety of other reagents may be included in the screening assay. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used.

The mixture of components may be added in any order that provides for the requisite binding.

Screening for agents that activate type 2 receptors is done in a manner similar to those outlined above. In addition, in some embodiments it may be desirable to prevent activation of the type 2 receptors, using the same basic assays described herein, but looking for agents that interfere with activation and/or internalization, i.e. an antagonist. For example, agents which bind to the activation sequences but do not allow multimerization of the receptors could be antagonists. However, as will be appreciated by those in the art, antagonists may be linked together, for example via covalent bonds, to provide for a "dimer" of the antagonist that now may act as an activator, since the dimer will now bind at least two receptors. This can be done using linkers as will be appreciated by those in the art.

In a preferred embodiment, methods of screening are provided. In this embodiment, candidate bioactive agent as defined above are added to a type 2 cell surface receptor with an activation sequence. The receptor may be on the surface of a cell, or may be done in vitro. The system is then assayed to determine whether the candidate bioactive agent binds to the activation sequence and activates the receptor.

Similarly, a preferred embodiment provides methods of screening comprising adding a candidate bioactive agent to a mammalian cell which has a type 2 cell surface receptor with an activation sequence. The system is then assayed to determine whether the candidate bioactive agent binds to the activation sequence and activates the receptor.

In this way, bioactive agents are identified. Compounds with pharmacological activity are able to enhance or interfere with the internalization of cell surface receptors in response to ligand binding, or can serve as ligand replacements as described herein. Binding to the site on the receptor corresponding to the subject oligopeptides is indicative of such activity, as is the ability to interfere with the binding of the subject oligopeptides to the cognate receptor. The compounds having the desired pharmacological activity may be administered in a physiologically acceptable carrier to a host, as previously described. The agents may be administered in a variety of ways, orally, parenterally e.g., subcutaneously, intraperitoneally, intravascularly, etc. Depending upon the manner of introduction, the compounds may be formulated in a variety of ways. The concentration of therapeutically active compound in the formulation may vary from about 0. 1–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

Accordingly, methods are provided for enhancing the physiological effect of ligand binding to cell surface receptors by administration of such bioactive, receptor derived oligopeptides, oligopeptide homodimers, and MHC/receptor oligopeptide heterodimers. The methods are used in diagnosis and therapy of diseases that involve inadequate or inappropriate receptor response. The data indicate that internalization of the receptor is inhibited by the presence of the subject oligopeptides, thereby providing for a greater number of receptors on the cell surface, and increased effectiveness of ligand binding. In addition, as outlined herein, the oligopeptides may also serve as ligand replacements.

In a preferred embodiment, the oligopeptides of the invention may be used to elucidate the function of unknown receptors, so called "orphan receptors". That is, for receptors for which no known function is associated, it is possible to add oligopeptides to the receptors, either in vivo or in vitro, and look for effects, as will be appreciated by those in the art.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

EXPERIMENTAL

Example 1

In order to determine the region on the external domain of a cell surface receptor that is involved in receptor internalization, a sequence similarity comparison was performed. The comparisons were performed with the commercially available Wisconsin Package, version 8.0-openVMS, Genetics Computer Group. The complete receptor sequences were obtained from public databases, as previously described in the "Database References for Nucleotide and Amino Acid Sequences". The similarity is based on the evolutionary distance between amino acids, as measured by Dayhoff and normalized by Gribskov and Burgess (1986) Nucl. Acids Res. 14:6745–6763. The "local homology" algorithm of Smith and Waterman (1981) *Advances in Applied Mathematics* 2:[482]–289 finds the best segments of similarity between the two sequences.

A similarity search between SEQ ID NO: 1 and amino acid sequences of the cell surface receptors outlined herein was done, and the regions outlined above were identified, as shown in the table below.

TABLE 1

Peptides-modulators of cognate receptor activity

| Receptor | Sequence | SEQ ID:NO |
|---|---|---|
| IR | KTDSQILKELEESSFRKTFEDYLH | SEQ ID:NO 3 |
| IGF-IR | [ERETQIAKGNEQSFRVDLRTLLR] KTEAEKQAEKEEAEYRKVFENFLH | SEQ ID:NO 5 |
| TPO-R | ARGGTLELRPRSRYRLQLRARLN | SEQ ID:NO 10 |
| EPO-R | QRVEILEGRTECVLSNLRGRTRY | SEQ ID:NO 11 |
| PDGF-R | EITTDVEKIQEIRYRSKLKLI | SEQ ID:NO 27 |
| VEGF-R | EARCDFCSNNEESFILDADSNM | SEQ ID:NO 28 |
| GH-R | EYELQYKEVNETKWKMMDPILTTSVPVY | SEQ ID:NO 9 |
| PRL-R | EWEIHFAGQQTEFKILSLHPGQKYL | SEQ ID:NO 35 |
| OB-R | KKENKIVPSKEIVWWMNLAEKIP | SEQ ID:NO 6 |
| EGF-R | GPHCVKTCPAGVMGENNTLVWKY | SEQ ID:NO 8 |
| LDL-R | EAEAAVATQETSTVRLKVSSTAVRT | SEQ ID:NO 4 |
| Tf-R | EKTDRFVMKKLNDRVMRVEYHFLSPY | SEQ ID:NO 34 |
| CNT-R | TWQTPSTWPDPESFPLKFFLRY | SEQ ID:NO 29 |
| GLUT-4 | [ERETQIAKGNEQSFRVDLRTLLR] TWLGROGPEGPSSIPPGTLTTLW | SEQ ID:NO 2 |
| TC-Ra | DSQTNVSQSKDSDVYITDKTVL | SEQ ID:NO 30 |

TABLE 1-continued

Peptides-modulators of cognate receptor activity

| Receptor | Sequence | SEQ ID:NO |
|---|---|---|
| TC-Rp | EWTQDRAKPVTQIVSAEAWGRADC | SEQ ID:NO 31 |
| TC-Rγ | SQEGNTMKTNDTYMKFSWLTVPEESLDKEHRCIVRH | SEQ ID:NO 32 |
| TC-Rδ | VHTEKVNMMSLTVLGLRMLF | SEQ ID:NO 33 |
| IL-2Rα | EMQSPMQPVDQASLPGHCREPPPW | SEQ ID:NO 12 |
| IL-2RP | DPDEGVAGAPTGSSPQPLQPL | SEQ ID:NO 13 |
| IL-3R | QEEGANTRAWRTSLLIALGTLL | SEQ ID:NO 14 |
| IL-4R | EPSLRIAASTLKSGISYRARVRAWAQCY | SEQ ID:NO 15 |
| IL-5R | DYETRITESKCVTILHKGFSASVRTILQ | SEQ ID:NO 16 |
| IL-6R | PAQEVARGVLTSLPGDSVTL | SEQ ID:NO 17 |
| IL-7R | GKSNICKVKVGEKSLTCKKIDLTTIVK | SEQ ID:NO 18 |
| IL-8Rα | EVLGNDTAKWRMVLRILPHTF | SEQ ID:NO 20 |
| IL-8RP | EDMGNNTANWRMILLRILPQSF | SEQ ID:NO 19 |
| IL-9R | ELDPGFIHEARLRVQMATL | SEQ ID:NO 21 |
| IL-IIR | EVITDAVAGLPHAVRVSARDFL | SEQ ID:NO 22 |
| IL-12R | EQPTQLELPEGCQGLAPGTEVTYRLQLHML | SEQ ID:NO 23 |
| IL-13Rα | KQDKKIAPETRRSIEVPLNERI | SEQ ID:NO 25 |
| IL-13RP | EWSDKQCWEGEDLSKKTLLRFW | SEQ ID:NO 24 |
| IL-17R | DPNITVETLEAHQLRVSFTLWNESTHYQILLTSF | SEQ ID:NO 26 |

TABLE 2

Similarity between MHC-I peptide and certain sequences on cell-surface receptors

| Receptor | Identity (%) | Similarity (%) |
|---|---|---|
| IR | 35 | 57 |
| IGF-IR | 32 | 55 |
| TPO-R | 22 | 44 |
| EPO-R | 26 | 44 |
| PDGF-R | 29 | 52 |
| VEGF-R | 27 | 50 |
| GH-R | 32 | 48 |
| PRL-R | 20 | 48 |
| OB-R | 18 | 48 |
| EGF-R | 17 | 44 |
| LDL-R | 16 | 88 |
| Tf-R | 29 | 54 |
| CNT-R | 27 | 59 |
| GLUT-4 | 13 | 39 |
| TC-Rα | 14 | 50 |
| TC-Rβ | 17 | 38 |
| TC-Rγ | 29 | 50 |
| TC-Rδ | 37 | 58 |
| IL-2Rα | 13 | 38 |
| IL-2Rβ | 19 | 38 |
| IL-3R | 27 | 50 |
| IL-4R | 28 | 52 |
| IL-5R | 40 | 52 |
| IL-6R | 30 | 50 |
| IL-7R | 26 | 61 |
| IL-8Rα | 19 | 52 |
| IL-8Rβ | 24 | 43 |
| IL-9R | 32 | 63 |
| IL-11R | 32 | 46 |
| IL-12R | 43 | 67 |
| IL-13Rα | 23 | 41 |
| IL-13Rβ | 27 | 59 |
| IL-17R | 24 | 52 |

Example 2

Methods

Insulin Receptor modification and expression. The human insulin receptor gene, as described in the database references and in Ebina et al. (1985) *Cell* 40:747–758) with a pCR3 expression vector (Invitrogen, catalog no. K3000–01) was transfected by electroporation into HeLa cells. Methods of electroporation are described in Boggs et al. (1986) *Ex. Hematol.* 149:988–994. In the transfected cells the receptors show insulin dependent internalization.

A mutated form of the insulin receptor was created by deleting residues 713 to 740 (SEQ ID NO:36; PKTDSQILKELEESSFRKTFEDYLHNV) using amplification primers that spanned the region to be deleted. The deletion mutant, mIR, was transfected into HeLa cells and internalization of the mIR was then tested.

Measurement of IR internalization. Receptor internalization was performed essentially as described in Stagsted et al. (1990) *Cell* 62:297–307. Briefly, 50 μl of the transfected cells at 106 cells/ml were incubated in a shaking water bath at 37° C. with 625 pM 125I-labeled insulin in the absence or presence of 10 μM of peptide as shown in Table 1, and the final volume brought to 100 μl. The cells were then diluted with 50 μl of KRHB (pH7.2) (no acid wash) or 50 μl of KRHB (pH 2.0) (acid wash) and incubated on ice for 5 min. The cells were finally harvested by centrifugation on top of silicone oil, and both free and cell-associated radioactivity was measured.

Glucose Transport in Adipose Cells. The biological activity of the peptides were measured by their effect on glucose uptake in rat adipose cells as described (Stagsted et al. (1991) *J. Biol. Chem.* 266:12844–12847). Briefly, rat adipose cells were obtained from epididymal fat pads and suspended in Krebs-Ringer HEPES buffer (KRH) with 5% bovine serum albumin at a lipocrit of 10% (final). The peptide effect was measured in cells maximally stimulated with insulin (10 nM). After equilibration at 37° C. for 30 min the cells were incubated for 30 min at 37° C. with buffer (basal), 10 nM insulin plus peptide. $^{14}$C-D-glucose was added, and the cells were incubated for an additional 30 min and harvested on oil. Biological activity was measured by a dose-response curve to interpolate the $EC_{50}$ value, taking the maximum enhancement of insulin effect (about 40% over the insulin-only maximum) as 100%. Most of the peptides were not tested at higher concentrations than 30 μM. Peptides that enhanced the maximum insulin effect by less than 20% at 30 μM were considered inactive.

Peptides. The peptides were assembled stepwise either on a phenylacetamidomethyl (PAM) resin using the t-Boc NMP/HOBt protocol of an Applied Biosystems Model 430A peptide synthesizer, or on a p-alkoxy benzyl alcohol (Wang) resin using a modified Fmoc/BOP protocol of a Milligen/Biosearch Model 9600 synthesizer. The desired peptides were confirmed by sequence analysis, amino acid composition, and fast atom bombardment mass spectrometry. The peptides were activated by incubation of 1 mM stock solution at 37° C. in 0.1 M NaCl overnight (Stagsted et al. (1991) *J. Biol. Chem.* 266:12844–12847).

Results

Effect of peptides on receptor internalization. The kinetics of internalization for insulin receptor and mutated insulin receptor were determined in the absence or presence of the peptides: SEQ ID NO:3, KTDSQILKELEESSFRKT-FEDYLH (pepIR) and SEQ ID NO:37, GNEQSFRVDL-RTLLRYAGGGNEQSFRVDLRTLLRYA (DS-A85). The data are shown in Table 2, where the numbers indicate percent internalized receptor.

TABLE 2

| Time (min) | IR | mIR | IR + DS-A85 | mIR + DS-A85 | IR + PEPIr | MIR + pepIR |
|---|---|---|---|---|---|---|
| 5 | 6 ± 4 | 4 ± 5 | 5 ± 4 | −1 ± 5 | 6 ± 4 | 5 ± 4 |
| 15 | 39 ± 7 | 2 ± 2 | 9 ± 6 | 0 ± 3 | 2 ± 2 | −2 ± 1 |
| 30 | 68 ± 6 | 4 ± 5 | 14 ± 6 | 2 ± 3 | 6 ± 4 | 0 ± 2 |
| 60 | 74 ± 8 | 5 ± 4 | 17 ± 3 | 1 ± 4 | 2 ± 4 | 2 ± 3 |

The data show that the mutated insulin receptor mIR does not internalize upon insulin binding, whereas more than 50% of the wild type IR is internalized within 30 minutes. The pepIR peptide inhibits receptor internalization to the same extent as DS-A85.

Effect of peptides on glucose uptake. At maximal insulin stimulation, the addition of pep1R did not significantly affect glucose uptake, indicating that pepIR does not affect GLUT4 internalization. Glucose uptake is enhanced 14±3 fold by the addition of 10 μM insulin. Insulin +10 μM of the DS-A85 peptide enhances glucose uptake 22±4 fold, whereas addition of insulin +10 μM pepIR enhances glucose uptake 12±4 fold, a result not significantly different from insulin alone.

The GLUT4pep (SEQ ID NO:2), at a concentration of 10 μM, does not affect insulin receptor internalization by the transfected cells. In the presence of peptide the per cent internalized receptor is 6±9, in the absence of peptide it is 64±7. The peptide does inhibit the internalization of GLUT4, as shown by the effect on glucose uptake at maximal insulin stimulation. In the presence of 10 nM insulin, the enhancement of glucose uptake was 12±4 fold. The enhancement was increased to 24±2 fold with the addition of the GLUT4pep. The peptide therefore seems to inhibit internalization of GLUT4, but not insulin receptor.

It is evident from the above results that oligopeptides having the sequence of the extracellular domain of a cell surface receptor, and having sequence identity with a region of an MHC class I antigen, are effective in inhibiting the internalization of the corresponding receptor. The peptides are therapeutically useful in enhancing the cellular response to hormones such as insulin.

Example 2

Ligand Replacement and Synergistic Addition Protocol for Protein Phosphorylation and Activation of Cognate Receptor Signaling Cascade Materials Appropriate cell lines have the following attributes: they are responsive to the appropriate hormone, they expresses the cognate receptor, they possess molecules required for down stream signaling of hormone induced response. The growth medium is as recommended for cell line.

Antibodies: Immunoprecipitation: 2–5 μg of Anti PY-99 (Santa Cruz Biotechnology), Anti-Receptor or signaling molecule specific antibody (e.g., Jak, STAT); Western blot: Anti Receptor specific antibody, Signaling protein specific antibody (Santa Cruz Biotechnology); or anti-PTyr (4G10, Upstate Biotech); with secondary antibody being appropriate according to the primary. Immunoprecipitation: Protein G beads (Pharmacia); 20–40 μl of slurry.

Protease inhibitor mix (100×) in water: 1 mg/ml Aprotinin, 0.1 mg/ml Pepsatin A, 0.1 mg/ml Leupeptin, 0.1 mg/ml Chymostatin, 0.1 mg/ml AEBSF.

Cell wash buffer: PBS with 1 mM ortho-vanadate, 50 mM NaF, 20 mM β-glycerophosphate and 2 mM sodium phyro-phosphate.

Lysis buffer: 50 mM HEPES, 150 mM NaCl, 1% Triton X-100, 1× protease inhibitor mix, 50 mM NaF, 5 mM EDTA, and 2 mM sodium phyrophosphate.

Blocking buffer: Blotto: TST (0.01 M Tris pH 7.4, 0.15 M NaCl, 0.075% Tween 20, 0.02% $NaN_3$)+0.5% Dry Skim Milk Powder Procedure Treatment of the Cells The cells were grown cells to an approximate density of $1 \times 10^6$ cells, centrifuged down and resuspended in recommended media for growth. The cells were starved for 14–18 hours at 37° C. (5% $CO_2$) in a media without serum, spun down and resuspended cells at a density of $1 \times 10^6$ cells/ml in a media without serum. 10 ml of cell suspension per P100 tissue culture dish was used. The cell suspension was treated with 0.01–30 μM peptide, 15–30 min at 37° C. (5% $CO_2$); (thaw peptide very shortly before the assay). 10 ml of ice cold cell wash buffer was added per dish, transfered to a Falcon tube and centrifuged down quickly at 4° C. and 3000 rpm. The media was carefully aspirated and the wash was repeated at 4° C.

The following steps were all performed on ice: The media was aspirated and 0.6 ml of 2×lysis buffer/tube was added. This was pipetted up and down and transfered to Eppendorf tubes, let sit on ice for ca. 30 min, and centrifuged at 14,000×g for 10 min, at 4° C. The supernatant (Lysate) was used in Immunoprecipitations.

Immunoprecipitation: The protein G beads were washed with 0.5×lysis buffer in Eppendorf tubes, 1–4 μg of Anti-PY-99 antibody was added, with receptor specific or signaling molecule (JAK2, STAT5) specific antibody per IP. The tubes were incubated with end-over-end rotation for 2 h at RT. The lysate was added, the tubes incubated with end-over-end rotation over night at 4° C. The beads were washed 3 times with 1×lysis buffer, 40 μl of SDS-sample buffer was added, and the samples were boiled for 3 min.

Western blot analysis: ca 12 μl/sample was run on 8% Polyacrylamide mini gel, transferred to PVDF-membrane (Millipore), blocked for 1 h in blocking buffer, incubated with the appropriate primary antibody 1:1000, o/n at 4° C. The membrane was washed, incubated with appropriate secondary-alk. phosphatase conjugated secondary antibody 1:2000, at RT for 2 hours. The PVDF-membrane was washed with Blotto and developed with NBT/BCIP.

Protocol for EPO-R Activation (Phosphorylation)

TF-1 cells from ATCC were used, with the growth medium being RPM1 1640 with 1×Penicillin/Streptomycin, 2 mM glutamin, 10% fetal bovine serum (Hyclone), and 1 ng/ml GM-CSF.

Treatment of the cells: Cells were grown to an approximate density of $1 \times 10^6$ cells, centrifuged down and resuspended in media with 5% serum and no GM-CSF. The cells were starved for 14–18 hours at 37° C. (5% $CO_2$), spun down and resuspended cells at a density of $1 \times 10^6$ cells/ml in a media without serum and GM-CSF. 10 ml of cell suspension per P100 tissue culture dish was used. The cell suspension was treated with 1–30 μM peptide, 15–30 min at 37° C. (5% $CO_2$); (thaw peptide very shortly before the assay). 10 ml of ice cold cell wash buffer was added per dish, transfered to Falcon tube and centrifuged down quickly at 4° C. and 3000 rpm. The media was carefully aspirated and the wash repeated at 4° C., with the following steps performed on ice: The media was aspirated and 0.6 ml of 2×lysis buffer/tube was added; this was pipetted up and down and transferred to Eppendorf tubes that sat on ice for ca. 30 min. The tubes were then centrifuged at 14,000×g for 10 min, at 4° C., and the supernatant (Lysate) removed and used in Immunoprecipitations and Western blots, as above, using anti-EPO-receptor antibody (Santa Cruz Biotechnology).

The results are shown in the Figures.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A composition of matter consisting of an activation sequence selected from the group consisting of SEQ ID NO:2; SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22; SEQ ID NO:23; SEQ ID NO:24; SEQ ID NO:25; SEQ ID NO:26; SEQ ID NO:27; SEQ ID NO:28; SEQ ID NO:29; SEQ ID NO:30; SEQ ID NO:31; SEQ ID NO:32; SEQ ID NO:33; SEQ ID NO:34; and SEQ ID NO:35.

2. A composition of matter according to claim 1, wherein said activation sequence is SEQ ID NO:3.

3. A composition of matter according to claim 1, wherein said activation sequence is SEQ ID NO:6.

4. A composition of matter according to claim 1, wherein said activation sequence is SEQ ID NO:9.

5. A composition of matter according to claim 1, wherein said activation sequence is SEQ ID NO:10.

6. A composition of matter according to claim 1, wherein said activation sequence is SEQ ID NO:11.

7. A composition comprising a cell having an internalizing cell-surface receptor in the membrane of said cell, said receptor having an activation sequence to which an exogenous polypeptide is non-covalently bound, said exogenous polypeptide is of from 8 to 40 amino acids, for each said cell-surface receptor said exogenous polypeptide comprises at least 8 amino acids having the same sequence as said activation sequence, which 8 amino acids is included in a sequence selected from the group consisting of SEQ ID NO:2; SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22; SEQ ID NO:23; SEQ ID NO:24; SEQ ID NO:25; SEQ ID NO:26; SEQ ID NO:27; SEQ ID NO:28; SEQ ID NO:29; SEQ ID NO:30; SEQ ID NO:31 SEQ ID NO:32; SEQ ID NO:33; SEQ ID NO:34; and SEQ ID NO:35, wherein the internalization of said cell-surface receptor is modulated as compared to the absence of said exogenous polypeptide.

8. A composition according to claim 7, wherein said activation sequence is SEQ ID NO:3.

9. A composition according to claim 7, wherein said activation sequence is SEQ ID NO:6.

10. A composition according to claim 7, wherein said activation sequence is SEQ ID NO:9.

11. A composition according to claim 7, wherein said activation sequence is SEQ ID NO:10.

12. A composition according to claim 7, wherein said activation sequence is SEQ ID NO:11.

* * * * *